United States Patent
Tanaka et al.

(10) Patent No.: US 9,215,974 B2
(45) Date of Patent: Dec. 22, 2015

(54) APPARATUS FOR OPTOMETRIC SELF-EXAMINATION, MANAGEMENT SERVER AND CONTACT LENS SELECTION SYSTEM

(71) Applicant: MENICON CO., LTD., Nagoya-shi, Aichi (JP)

(72) Inventors: Hidenari Tanaka, Nagoya (JP); Masahiro Okawa, Kasugai (JP); Kensuke Muraki, Inuyama (JP)

(73) Assignee: MENICON CO., LTD., Nagoya-shi (JP)

( * ) Notice: Subject to any disclaimer, the term of this patent is extended or adjusted under 35 U.S.C. 154(b) by 0 days.

(21) Appl. No.: 14/311,073

(22) Filed: Jun. 20, 2014

(65) Prior Publication Data

US 2014/0300860 A1    Oct. 9, 2014

Related U.S. Application Data

(63) Continuation of application No. PCT/JP2011/079569, filed on Dec. 20, 2011.

(51) Int. Cl.
  *A61B 3/02* (2006.01)
  *A61B 3/10* (2006.01)
  *A61B 3/00* (2006.01)
  (Continued)

(52) U.S. Cl.
  CPC .............. *A61B 3/0025* (2013.01); *A61B 3/107* (2013.01); *A61B 3/18* (2013.01)

(58) Field of Classification Search
  USPC .................................................. 351/200–246
  See application file for complete search history.

(56) References Cited

U.S. PATENT DOCUMENTS

2002/0103673 A1* 8/2002 Atwood ............................ 705/2
2006/0023163 A1   2/2006 Foster
(Continued)

FOREIGN PATENT DOCUMENTS

JP    A-03-063027    3/1991
JP    A-2004-078675  3/2004
(Continued)

OTHER PUBLICATIONS

International Preliminary Report on Patentability issued in International Patent Application No. PCT/JP2011/079569 dated Jun. 24, 2014.
(Continued)

*Primary Examiner* — Mohammed Hasan
(74) *Attorney, Agent, or Firm* — Oliff PLC

(57) ABSTRACT

An object of the present invention is to provide an apparatus for optometric self-examination, a management server and a contact lens selection system using the same that are readily available to a new user and additionally shorten a time period required by an eye care practitioner for prescription or, even if no eye care practitioner's prescription is provided, allow for selection of a contact lens preferred for the user. The apparatus for optometric self-examination includes an optometric data acquisition unit for determining at least a part of a shape of a cornea of a user in response to an operation by the user and acquiring optometric data, based on the shape of the cornea, and a contact lens data display unit for displaying a result of selection of a contact lens suited for the optometric data, based on the optometric data and the shape data of contact lenses.

20 Claims, 12 Drawing Sheets

(51) Int. Cl.
*A61B 3/18* (2006.01)
*A61B 3/107* (2006.01)

(56) References Cited

U.S. PATENT DOCUMENTS

2006/0152675 A1* 7/2006 Toshima et al. ............... 351/205
2010/0302509 A1 12/2010 Steinmüller

FOREIGN PATENT DOCUMENTS

JP  A-2008-508006  3/2008
JP  A-2011-036645  2/2011

OTHER PUBLICATIONS

International Search Report issued in International Application No. PCT/JP2011/079569 dated Mar. 19, 2012 (with translation).

* cited by examiner

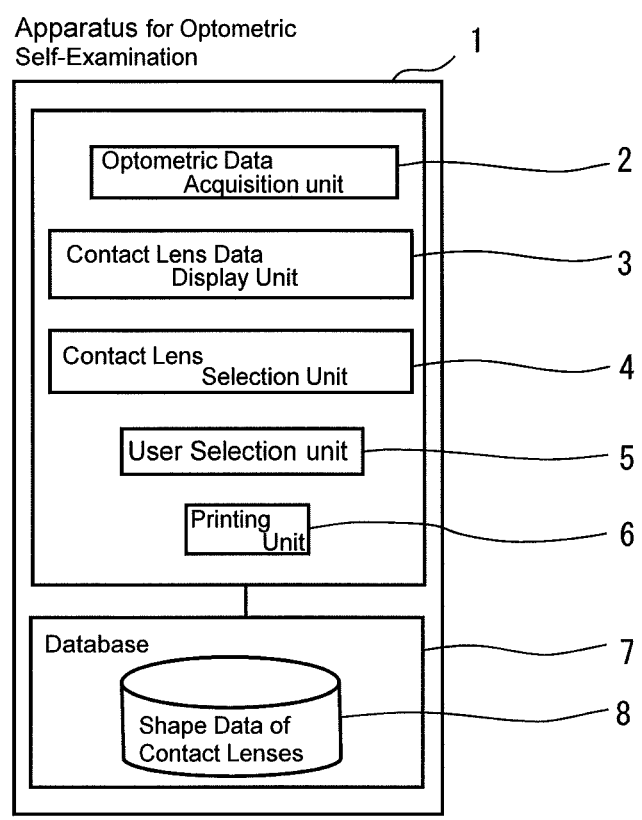
F I G. 1

025# APPARATUS FOR OPTOMETRIC SELF-EXAMINATION, MANAGEMENT SERVER AND CONTACT LENS SELECTION SYSTEM

This is a Continuation of International Application No. PCT/JP2011/079569 filed Dec. 20, 2011. The disclosure of the prior application[s] is hereby incorporated by reference herein in its entirety.

TECHNICAL FIELD

The present invention relates to an apparatus for optometric self-examination, a management server and a contact lens selection system which are suitable for easy and favorable selection of a contact lens.

BACKGROUND ART

Conventionally, contact lenses have been used to correct various vision conditions such as myopia, hyperopia, astigmatism and presbyopia. Moreover, the contact lenses include hard contact lenses, which have a small lens diameter and can be used for a comparatively long period of time, and soft contact lenses (including disposable type contact lenses), which have a large lens diameter and can be placed comparatively easily. When optimal contact lenses are selected depending on a user's preference and/or adaptability, the contact lenses can lead to appropriate correction of the user's vision without causing any stress such as a feeling of unpleasantness or discomfort upon wearing of the contact lenses.

When a user purchases such contact lenses, a process including the following procedures is typically performed:

(1) the user visits a contact lens store, and receives an explanation of contact lenses and guidance on a clinic;

(2) the user visits the clinic, applies at an information desk of the clinic, and is interviewed in regard to the type of a preferred contact lens, a past history of the user, presence or absence of allergies, a use of an eye drop, and the like;

(3) an eye care practitioner executes examinations such as an examination of the anterior segment and/or the fundus of the eye, an objective refraction, a subjective refraction and a measurement of the radius curvature of the cornea, and the eye care practitioner selects the specification of contact lenses suitable for the user at the eye care practitioner's discretion;

(4) a trial lens is placed on the user's eye, and the specification such as a curvature, a dioptric power and a diameter of the lens is determined;

(5) the eye care practitioner checks a state of the user wearing the lens, and the like, and issues an instruction; and (6) the user presents the instruction to a store, and purchases contact lenses in accordance with the instruction; and the like.

Also, ordering contact lenses for a second and the following times often includes similar procedures.

According to such a process of purchasing contact lenses, for the user to purchase contact lenses, it is necessary to follow a process in which the user visits a contact lens store, is introduced to a clinic, undergoes various examinations such as an examination of the anterior segment and/or the fundus of the eye, an objective refraction, a subjective refraction and a measurement of the radius curvature of the cornea in the clinic, and thereafter receives an instruction issued by an eye care practitioner in the clinic.

However, user candidates and the like who are hesitating as to whether the user should use a contact lens or not are likely to feel such a process to be cumbersome. Therefore, some users and user candidates disfavor such procedures and abandon purchase of contact lenses, and thus a widespread use of contact lenses seems to have been hampered.

In addition, in recent years, soft contact lenses, disposable contact lenses in particular, become widely used. Along with the widespread use of soft contact lenses, a decrease of opportunities of prescriptions for hard contact lenses is pronounced, and lowering of a technical level of eye care practitioners caused by this decrease is found. As a result, cases where even though an eye care practitioner is supposed to prescribe hard contact lenses, the eye care practitioner evades selection of optimal contact lenses and recommends soft contact lenses are concerned.

In order to solve such disadvantageous problems, for example, utilization of a system for selling a medical supply has been proposed (see Japanese Unexamined Patent Application, Publication No. 2004-78675). According to the system for selling a medical supply, since a terminal of a medical institution has a database to store electronic medical records of a user, a prescription for the user can be prepared based on retrieved data from the database. Therefore, a simplification of prescribing procedures can be expected.

However, even if the system for selling a medical supply is used, a new user needs to visit an eye care practitioner and undergo prerequisite examinations for contact lens selection; therefore, the system is less likely to promote a diffusion of the contact lens to new users. Moreover, even if the system for selling a medical supply is used, there is still a possibility that a specific type of contact lenses (for example, hard contact lenses) is not recommended due to lack of an eye care practitioner's skill and the like, and accordingly there is still a concern that a prescription of contact lenses optimal for a user may fail.

PRIOR ART DOCUMENTS

Patent Documents

Patent Document 1: Japanese Unexamined Patent Application, Publication No. 2004-78675

SUMMARY OF THE INVENTION

Problems to be Solved by the Invention

The present invention was made in view of the foregoing circumstances, and an object of the present invention is to provide an apparatus for optometric self-examination that is readily available to a new user, and additionally shortens a time period required by an eye care practitioner for prescription, or allows for selection of a contact lens preferred for the user even if no eye care practitioner's prescription is provided. Another object of the present invention is to provide a management server, and a contact lens selection system that includes the apparatus for optometric self-examination and the management server.

Means for Solving the Problems

According to an aspect of the invention made for solving the aforementioned problems, an apparatus for optometric self-examination is provided, including:

an optometric data acquisition unit for determining at least a part of a shape of a cornea of a user (including a user candidate, the term "user" as used hereinafter may correctively mean "user and user candidate") in response to an operation by the user and acquiring optometric data, based on the shape of the cornea; and a contact lens data display unit for displaying a result of selection of a contact lens suited for the optometric data, based on the optometric data and shape data of contact lenses.

According to the apparatus for optometric self-examination, the optometric data acquisition unit acquires the optometric data in response to an operation by the user, and the contact lens data display unit enables data of a contact lens (hereinafter, may be also referred to as "contact lens data") suited for the optometric data to be displayed. Accordingly, the apparatus for optometric self-examination is readily available to even a new user through the user's own operation, and the user can find a contact lens suitable for the user. In addition, according to the apparatus for optometric self-examination, when an eye care practitioner uses the optometric data and the contact lens data displayed by the contact lens data display unit, a time period required by the eye care practitioner for prescription can be shortened. The term "eye care practitioner" or "practitioner" as used herein refers appropriately to anyone qualified to fit, prescribe, or dispense vision correction devices such as contact lenses, spectacles and the like, or medically attend to a patient particularly with respect to the patient's eyes.

The apparatus for optometric self-examination preferably includes a database to store shape data of a plurality of contact lenses; and a contact lens selection unit for selecting one or a plurality of contact lenses suited for the optometric data, based on the optometric data and shape data of contact lenses stored in the database. The apparatus for optometric self-examination can select a contact lens suitable for the user via the contact lens selection unit. According to the apparatus for optometric self-examination, the contact lens selection unit selects one or a plurality of contact lenses suited for the user based on the shape data of a plurality of contact lenses stored in the database; therefore the database storing shape data of various contact lenses such as soft contact lenses and hard contact lenses enables lack of an eye care practitioner's skill to be favorably compensated for, and thus a contact lens suitable for the user can be provided.

It is preferred that the optometric data acquisition unit acquires curvature data at a plurality of points on a surface of the cornea of the user as the optometric data, and the contact lens selection unit calculates an average value from the maximum value and the minimum value among the curvature data at the plurality of points acquired as the optometric data and selects the one or a plurality of contact lenses based on the average value. Accordingly, by obtaining the curvature data at a plurality of points on the surface of the cornea of the user, a contact lens suitable for the user can be easily and rapidly selected.

It is preferred that the contact lens selection unit selects the one or a plurality of contact lenses after making a correction based on a value obtained by subtracting the minimum value from the maximum value among the curvature data at the plurality of points acquired as the optometric data. Accordingly, fitting properties of the selected contact lens to the user can be improved.

It is preferred that the optometric data acquisition unit acquires data of the corneal shape of the user (hereinafter, may be also referred to as "corneal shape data") as the optometric data, and the contact lens selection unit calculates a distance from a cornea surface to a back face of the contact lens along a normal direction, based on the corneal shape data and the shape data of contact lenses, and select the one or a plurality of contact lenses based on the distance along the normal direction. Accordingly, fitting properties of the selected contact lens to the user can be further improved.

It is preferred that the optometric data acquisition unit acquires data of a refractive index of the eye of the user (hereinafter, may be also referred to as "eye refractive index data"), and the contact lens selection unit determines a dioptric power of the contact lenses based on the data of the refractive index of the eye. Accordingly, a dioptric power of a contact lens suitable for the user can be easily and rapidly determined.

It is preferred that the contact lens selection unit calculates spatial data of a space formed between a surface of the cornea of the user and a back face of the contact lens, based on the optometric data and the shape data of contact lenses, thereafter acquires data of a lacrimal fluid layer formed between the surface of the cornea of the user and the back face of the contact lens, based on the spatial data, and determines the dioptric power of the contact lens in light of a shape of the lacrimal fluid layer. Accordingly, accuracy of the dioptric power of the contact lenses selected by the contact lens selection unit can be further improved.

It is preferred that the contact lens data display unit displays a fluorescein pattern representing the shape of the lacrimal fluid layer. Accordingly, the user can ascertain the fluorescein pattern without using a trial lens. Moreover, according to such a constitution, the user can visually ascertain fitting properties of the contact lens, and consequently a comfort level of the user can be enhanced.

It is preferred that the contact lens selection unit calculates a refraction value of the contact lens in a state of the contact lens being applied to the eye (over-refraction value) based on the optometric data, the spatial data and shape data of the contact lens selected, and the contact lens data display unit displays the over-refraction value. Accordingly, validity of the contact lenses selected by the contact lens selection unit can be displayed to the user, and consequently a comfort level of the user can be enhanced.

It is preferred that the contact lens selection unit simulates visual performances in use of the contact lens based on the over-refraction value, and the contact lens data display unit displays a result of simulation of the visual performances. Accordingly, validity of the contact lenses selected by the contact lens selection unit can be displayed to the user, and a comfort level of the user can be further enhanced.

It is preferred that the optometric data acquisition unit acquires data of a transverse corneal diameter of the user, and the contact lens selection unit determines a diameter of the contact lens based on the data of the transverse corneal diameter. Accordingly, the diameter of the contact lens suitable for the user can be easily and rapidly selected.

It is preferred that the apparatus for optometric self-examination includes a contact lens type reception unit for receiving an input of a contact lens type desired by the user, and the contact lens selection unit selects the one or a plurality of contact lenses that match the contact lens type received by the contact lens type reception unit. Accordingly, it is possible to select a contact lens in accordance with preference of the user.

It is preferred that the contact lens data display unit displays data of a plurality of contact lenses, and the apparatus for optometric self-examination includes a user selection unit for allowing the user to select any contact lens from among the plurality of contact lenses the data of which are displayed by the contact lens data display unit. Accordingly, a contact lens suitable for and preferred by the user can be easily selected.

It is preferred that the apparatus for optometric self-examination includes an affiliated facility display unit for displaying data of a plurality of affiliated facilities capable of prescribing a contact lens, and a prescription requesting unit for allowing the user to select any affiliated facility from among the affiliated facilities displayed by the affiliated facility display unit and requesting for a prescription with the affiliated facility in response to an operation by the user. Accordingly, the user obtains the optometric data and data of the contact lenses suited for the optometric data from the apparatus for optometric self-examination, and then can request for a prescription with an affiliated facility along with an appointment of a desired date and time. Therefore, according to the apparatus for optometric self-examination, since the user can visit the affiliated facility at convenience to the user, a time period required for prescription in the affiliated facility can be shortened by utilizing the data obtained from the apparatus for optometric self-examination, and additionally, a closer and more detailed prescription can be provided by the affiliated facility. Moreover, according to the apparatus for optometric self-examination, the affiliated facility can gain the benefit of favorably compensating for lack of skill by utilizing the data obtained from the apparatus for optometric self-examination.

It is preferred that the apparatus for optometric self-examination includes a printing unit for printing the optometric data acquired by the optometric data acquisition unit, and data of the one or a plurality of contact lenses selected by the contact lens selection unit. Accordingly, the user can easily acquire user's own optometric data and data of contact lenses suitable for the user and keep these data on hand. Therefore, according to the apparatus for optometric self-examination, the user can ascertain the user's own optometric data and the data of the contact lenses suitable for the user any time. Furthermore, according to the apparatus for optometric self-examination, the user can visit a contact lens store and the like with these data held in the user's hand and purchase desired contact lens(es), or alternatively can visit an eye care practitioner and the like with these data held in the user's hand and receive a closer and more detailed prescription.

It is preferred that the apparatus for optometric self-examination includes a prescription data recording unit for recording a correlation between the data of the contact lenses selected by the contact lens selection unit and data of the prescription executed by the affiliated facility that received the request from the prescription requesting unit, and the contact lens selection unit selects the one or a plurality of contact lenses after making a correction based on the data recorded by the prescription data recording unit. According to the apparatus for optometric self-examination, the prescription data recording unit records the data of the contact lenses selected by the contact lens selection unit and data of a contact lens prescribed in the affiliated facility that received the request from the prescription requesting unit. Therefore, the apparatus for optometric self-examination can determine an error bound for the contact lens selection unit from a difference between the data of the contact lenses selected by the contact lens selection unit and the data of the contact lens prescribed in the affiliated facility that received the request from the prescription requesting unit. Accordingly, the apparatus for optometric self-examination can improve fitting properties of the selected contact lens, since the contact lens selection unit makes a correction based on such an error.

It is preferred that the prescription data recording unit records the data of the contact lenses selected by the contact lens selection unit and the data of the prescription executed by the affiliated facility, in relationship to user identification data, and the contact lens selection unit makes a correction with respect to each user based on the data recorded by the prescription data recording unit. Accordingly, so far as a user who uses the apparatus for optometric self-examination more than once is concerned, fitting properties of the contact lenses selected by the contact lens selection unit can be further improved.

It is preferred that the apparatus for optometric self-examination includes an optometric data transmission unit for transmitting via a network the optometric data acquired by the optometric data acquisition unit, in relationship to the user identification data. The apparatus for optometric self-examination can transmit the optometric data and the user identification data to an external apparatus capable of communicating with the apparatus for optometric self-examination via a network using the optometric data transmission unit. As a result, using such an external apparatus, the apparatus for optometric self-examination can select a contact lens suitable for the user.

It is preferred that the apparatus for optometric self-examination includes a prescription-related data transmission unit for transmitting via a network the optometric data acquired by the optometric data acquisition unit and the data of the contact lenses selected by the contact lens selection unit, as prescription-related data, in relationship to the user identification data. According to the apparatus for optometric self-examination, the prescription-related data transmission unit can transmit via a network the prescription-related data. Therefore, according to the apparatus for optometric self-examination, an eye care practitioner or the like who prescribes for the user can receive the prescription-related data transmitted by the prescription-related data transmission unit on a predetermined apparatus, and thereafter prescribe a contact lens using the prescription-related data. Accordingly, the apparatus for optometric self-examination enables a time period required by an eye care practitioner for prescription to be shortened, and additionally more detailed prescription may be provided by the eye care practitioner. Moreover, the apparatus for optometric self-examination also enables a contact lens suitable for the user to be selected or obtained without a need of prescription by an eye care practitioner, based on the prescription-related data transmitted by the prescription-related data transmission unit. Furthermore, if the apparatus for optometric self-examination is configured to transmit the prescription-related data to a personal computer possessed by the user and the like, the apparatus for optometric self-examination enables the user to readily make viewing, management and the like by him/herself of the optometric data and data of contact lenses as well as changes of the optometric data and the data of the contact lens and the like, and consequently can enhance the user's awareness of information on the user's own eye.

In addition, according to another aspect of the invention made for solving the aforementioned problems, a management server capable of communicating with the apparatus for optometric self-examination via a network according to the aspect of the present invention is provided, the management server including:

a prescription-related data reception unit for receiving the optometric data as well as data of the contact lenses selected based on the optometric data and the shape data of contact lenses as the prescription-related data, in relationship to user identification data; and a prescription instruction data transmission unit for transmitting via a network, prescription instruction data produced based on the prescription-related data received by the prescription-related data reception unit.

According to the management server, the prescription instruction data transmission unit can transmit via a network the prescription instruction data produced based on the prescription-related data received by the prescription-related data reception unit. Therefore, according to the management server, provided that an eye care practitioner or the like who makes a prescription utilizes the prescription instruction data transmitted by the prescription instruction data transmission unit, a time period required for the prescription for the user can be shortened, and additionally a closer and more detailed prescription can be provided for the user. Moreover, the management server also enables a contact lens suitable for the user to be selected or obtained without a need of prescription by an eye care practitioner, by way of transmission of the prescription instruction data to a predetermined contact lens store and the like.

In addition, a management server capable of communicating with the apparatus for optometric self-examination via a network is provided, the management server including: a database to store shape data of a plurality of contact lenses; an optometric data reception unit for receiving the optometric data and the user identification data transmitted from the apparatus for optometric self-examination; a contact lens selection unit for selecting one or a plurality of contact lenses suited for the optometric data, based on the optometric data and the shape data of contact lenses stored in the database; and a first contact lens data transmission unit for transmitting data of the contact lenses selected by the contact lens selection unit to the apparatus for optometric self-examination. The management server can select one or a plurality of contact lenses suited for the user based on the shape data of a plurality of contact lenses stored in the database. The management server can favorably compensate for lack of an eye care practitioner's skill by storing in the database shape data of various contact lenses such as soft contact lenses and hard contact lenses, and can provide a contact lens suitable for the user.

According to the management server, it is preferred that the optometric data reception unit receives curvature data at a plurality of points on the surface of the cornea of the user, and the contact lens selection unit calculates an average value from the maximum value and the minimum value among the curvature data at the plurality of points and selects the one or a plurality of contact lenses based on the average value. Accordingly, by obtaining the curvature data at a plurality of points on the surface of the cornea of the user, a contact lens suitable for the user can be easily and rapidly selected.

According to the management server, it is preferred that the contact lens selection unit selects the one or a plurality of contact lenses after making a correction based on a value obtained by subtracting the minimum value from the maximum value among the curvature data at the plurality of points acquired as the optometric data. Accordingly, fitting properties of the selected contact lens to the user can be improved.

According to the management server, it is preferred that the optometric data reception unit receives corneal shape data of the user, the contact lens selection unit calculates a distance from cornea surface to a back face of the contact lens along a normal direction based on the corneal shape data and the shape data of contact lenses, and select the one or a plurality of contact lenses, based on the distance along the normal direction. Accordingly, fitting properties of the selected contact lens to the user can be further improved.

According to the management server, it is preferred that the optometric data reception unit receives eye refractive index data of the user, and the contact lens selection unit determines a dioptric power of the contact lens based on the eye refractive index data. Accordingly, the dioptric power of a contact lens suitable for the user can be easily and rapidly determined.

According to the management server, it is preferred that the contact lens selection unit calculates spatial data of a space formed between the surface of the cornea of the user and a back face of the contact lens, based on the optometric data and the shape data of contact lenses, thereafter acquires data of a lacrimal fluid layer formed between the surface of the cornea of the user and the back face of the contact lens, based on the spatial data, and determines a dioptric power of the contact lens in light of a shape of the lacrimal fluid layer. Accordingly, accuracy of the dioptric power of the contact lenses selected by the contact lens selection unit can be further improved.

According to the management server, it is preferred that the first contact lens data transmission unit transmits a fluorescein pattern representing the shape of the lacrimal fluid layer to the apparatus for optometric self-examination. The management server enables the user to visually recognize the fluorescein pattern transmitted by the first contact lens data transmission unit by allowing the apparatus for optometric self-examination that has received the fluorescein pattern transmitted by the first contact lens data transmission unit to display the fluorescein pattern. As a result, according to the management server, the user can ascertain the fluorescein pattern without using a trial lens. Moreover, according to such a constitution, the user can visually ascertain fitting properties of the contact lens, and consequently a comfort level of the user can be enhanced.

According to the management server, it is preferred that the contact lens selection unit calculates a refraction value in a state of the contact lens being applied to the eye (over-refraction value) based on the optometric data, the spatial data and the shape data of the contact lens selected, and the first contact lens data transmission unit transmits the over-refraction value to the apparatus for optometric self-examination. Accordingly, the over-refraction value can be displayed by means of the apparatus for optometric self-examination that has received the over-refraction value transmitted by the first contact lens data transmission unit. As a result, the management server can display validity of the contact lenses selected by the contact lens selection unit to the user, and consequently a comfort level of the user can be enhanced.

According to the management server, it is preferred that the contact lens selection unit simulates visual performances in use of the contact lens based on the over-refraction value, and the first contact lens data transmission unit transmits data of a result of simulation of the visual performances to the apparatus for optometric self-examination. Accordingly, a result of the simulation can be displayed by means of the apparatus for optometric self-examination that has received the data of the result of the simulation transmitted by the first contact lens data transmission unit. As a result, the management server can further enhance a comfort level of the user.

According to the management server, it is preferred that the optometric data reception unit receives data of a transverse corneal diameter of the user, and the contact lens selection unit determines a diameter of the contact lens based on the data of the transverse corneal diameter. Accordingly, the diameter of a contact lens suitable for the user can be easily and rapidly selected.

It is preferred that the management server includes contact lens type data reception unit for receiving contact lens type data of a contact lens desired by the user, and the contact lens selection unit selects the one or a plurality of contact lenses that match the contact lens type data. Accordingly, it is possible to select a contact lens in accordance with preference of the user.

It is preferred that the management server includes a prescription instruction data transmission unit for transmitting via a network, prescription instruction data produced based on the optometric data and the data of the contact lenses selected by the contact lens selection unit. Accordingly, easiness, preciseness and rapidity of the prescription of the contact lens can be improved.

According to still another aspect of the invention made for solving the aforementioned problems, a contact lens selection system is provided, including:
  an apparatus for optometric self-examination; and
  a management server capable of communicating with the apparatus for optometric self-examination via a network,
  the apparatus for optometric self-examination including:
    an optometric data acquisition unit for determining at least a part of a shape of a cornea of a user in response to an operation by the user and acquiring optometric data, based on the shape of the cornea;
    an optometric data transmission unit for transmitting the optometric data acquired by the optometric data acquisition unit to the management server in relationship to user identification data;
    a first contact lens data reception unit for receiving data of contact lenses selected based on the optometric data and shape data of contact lenses from the management server; and
    a contact lens data display unit for displaying the data of contact lenses received by the first contact lens data reception unit, and
  the management server including:
    a database to store shape data of a plurality of contact lenses;
    an optometric data reception unit for receiving the optometric data and the user identification data transmitted by the optometric data transmission unit;
    a contact lens selection unit for selecting one or a plurality of contact lenses suited for the optometric data, based on the optometric data and the shape data of contact lenses stored in the database; and
    a first contact lens data transmission unit for transmitting data of the contact lenses selected by the contact lens selection unit to the apparatus for optometric self-examination.

The contact lens selection system is readily available to even a new user through the user's own operation, and the user can find a contact lens suitable for the user. Moreover, when an eye care practitioner uses the optometric data and the contact lens data displayed by the contact lens data display unit, the contact lens selection system can shorten a time period required by the eye care practitioner for prescription. According to the contact lens selection system, since the contact lens selection unit selects one or a plurality of contact lenses suited for the user based on the shape data of a plurality of contact lenses stored in the database, the contact lens selection system can favorably compensate for lack of an eye care practitioner's skill by storing in the database shape data of various contact lenses such as soft contact lenses and hard contact lenses, and a contact lens suitable for the user can be provided.

According to the contact lens selection system, it is preferred that the contact lens data display unit displays data of a plurality of contact lenses, the apparatus for optometric self-examination includes a user selection unit for allowing the user to select any contact lens from among the plurality of contact lenses the data of which are displayed by the contact lens data display unit; and a second contact lens data transmission unit for transmitting the data of the contact lenses selected by the user selection unit to the management server in relationship to the user identification data, and the management server includes a second contact lens data reception unit for receiving the data of the contact lenses and the user identification data transmitted by the second contact lens data transmission unit. Accordingly, a contact lens suitable for the user and preferred by the user can be easily selected.

According to the contact lens selection system, it is preferred that the apparatus for optometric self-examination further includes a printing unit for printing the optometric data acquired by the optometric data acquisition unit and the data of the contact lenses received by the first contact lens data reception unit. Accordingly, the user can easily acquire the user's own optometric data and data of contact lenses suitable for the user, and keep these data on hand. Therefore, according to the contact lens selection system, the user can ascertain the user's own optometric data and the data of a contact lens suitable for the user any time. Furthermore, according to the contact lens selection system, the user can visit a contact lens store and the like with these data held in the user's hand and purchase desired contact lenses, or alternatively can visit an eye care practitioner and the like with these data held in the user's hand and receive more detailed prescription.

According to yet still another aspect of the invention made for solving the aforementioned problems, a contact lens selection system is also provided, including:
  an apparatus for optometric self-examination;
  a management server capable of communicating with the apparatus for optometric self-examination via a network; and
  a plurality of affiliated facility terminals capable of communicating with the apparatus for optometric self-examination and the management server via a network,
  the apparatus for optometric self-examination including:
    a database to store shape data of a plurality of contact lenses;
    an optometric data acquisition unit for determining at least a part of a shape of a cornea of a user in response to an operation by the user and acquiring optometric data, based on the shape of the cornea;
    a contact lens selection unit for selecting one or a plurality of contact lenses suited for the optometric data, based on the optometric data and the shape data of contact lenses stored in the database;
    a contact lens data display unit for displaying data of the contact lenses selected by the contact lens selection unit; and
    a prescription-related data transmission unit for transmitting the optometric data acquired by the optometric data acquisition unit and data of the contact lenses selected by the contact lens selection unit to the management server as prescription-related data, in relationship to user identification data, and
  the management server including:
    a prescription-related data reception unit for receiving the prescription-related data transmitted by the prescription-related data transmission unit; and
    a prescription instruction data transmission unit for transmitting prescription instruction data produced based on the prescription-related data received by the prescription-related data reception unit to an affiliated facility terminal in an affiliated facility in which a prescription is executed, and
  the affiliated facility terminal in the affiliated facility in which a prescription is executed including:
    a prescription instruction data reception unit for receiving prescription instruction data transmitted by the prescription instruction data transmission unit.

The contact lens selection system is readily available to even a new user through the user's own operation, and the user can find a contact lens suitable for the user. According to the contact lens selection system, since the contact lens selection unit selects one or a plurality of contact lenses suited for the user based on the shape data of a plurality of contact lenses stored in the database, the contact lens selection system can favorably compensate for lack of an eye care practitioner's skill by storing in the database shape data of various contact lenses such as soft contact lenses and hard contact lenses, and can provide a contact lens suitable for the user. According to the contact lens selection system, if an affiliated facility in which a prescription is executed utilizes the prescription instruction data transmitted by the prescription instruction data transmission unit, a reduction of a time period required for the prescription for the user and sophistication of the prescription for the user can be achieved, and additionally a process of purchase of a contact lens by the user can proceed smoothly.

In addition, according to further aspect of the invention, a contact lens selection system is provided that includes an apparatus for optometric self-examination; a management server capable of communicating with the apparatus for optometric self-examination via a network; and a plurality of affiliated facility terminals capable of communicating with the apparatus for optometric self-examination and the management server via a network, the apparatus for optometric self-examination including an optometric data acquisition unit for determining at least a part of a shape of a cornea of a user in response to an operation by the user and acquiring optometric data, based on the shape of the cornea; an optometric data transmission unit for transmitting the optometric data acquired by the optometric data acquisition unit to the management server in relationship to user identification data; a first contact lens data reception unit for receiving data of contact lenses selected based on the optometric data and the shape data of contact lenses from the management server; and a contact lens data display unit for displaying the data of one or a plurality of contact lenses received by the first contact lens data reception unit, the management server including a database to store shape data of a plurality of contact lenses; an optometric data reception unit for receiving the optometric data and the user identification data transmitted by the optometric data transmission unit; a contact lens selection unit for selecting one or a plurality of contact lenses suited for the optometric data, based on the optometric data and the shape data of contact lenses stored in the database; a first contact lens data transmission unit for transmitting the data of the contact lenses selected by the contact lens selection unit to the apparatus for optometric self-examination; and a prescription instruction data transmission unit for transmitting prescription instruction data produced based on the optometric data received by the optometric data reception unit and the data of the contact lenses selected by the contact lens selection unit to an affiliated facility terminal in an affiliated facility in which a prescription is executed, the affiliated facility terminal in the affiliated facility in which a prescription is executed including a prescription instruction data reception unit for receiving the prescription instruction data transmitted by the prescription instruction data transmission unit. The contact lens selection system is readily available to even a new user through the user's own operation, and the user can find a contact lens suitable for the user. According to the contact lens selection system, since the contact lens selection unit selects one or a plurality of contact lenses suited for the user based on the shape data of a plurality of contact lenses stored in the database, the contact lens selection system can favorably compensate for lack of an eye care practitioner's skill by storing in the database shape data of various contact lenses such as soft contact lenses and hard contact lenses, and a contact lens suitable for the user can be provided. According to the contact lens selection system, if an affiliated facility in which a prescription is executed utilizes the prescription instruction data transmitted by the prescription instruction data transmission unit, a reduction of a time period required for the prescription for the user and sophistication of the prescription for the user can be achieved, and additionally a process of purchase of a contact lens by the user can proceed smoothly.

According to the contact lens selection system, it is preferred that the contact lens data display unit displays data of a plurality of contact lenses, the apparatus for optometric self-examination further includes a user selection unit for allowing the user to select any contact lens from among the plurality of contact lenses the data of which are displayed by the contact lens data display unit; and a second contact lens data transmission unit for transmitting data of the contact lenses selected by the user selection unit to the management server in relationship to the user identification data, the management server further includes a second contact lens data reception unit for receiving the data of the contact lenses and the user identification data transmitted by the second contact lens data transmission unit, and the prescription instruction data transmission unit transmits prescription instruction data produced in light of the data of the contact lenses received by the second contact lens data reception unit. Accordingly, the contact lens selection system can produce prescription instruction data in light of the user's preference and thereafter transmit prescription instruction data to an affiliated facility. Therefore, according to the contact lens selection system, the affiliated facility can easily select a contact lens in light of the user's preference.

According to the contact lens selection system, it is preferred that the apparatus for optometric self-examination further includes an affiliated facility display unit for displaying data of affiliated facilities associated with the affiliated facility terminal; and a prescription requesting unit for allowing the user to select any affiliated facility from among the affiliated facilities displayed by the affiliated facility display unit and requesting for a prescription with the affiliated facility in response to an operation by the user. Accordingly, the user can request for a prescription with an affiliated facility along with an appointment of a desired date and time. According to the contact lens selection system, the affiliated facility that received the prescription request from the prescription requesting unit utilizes the prescription instruction data received by the prescription instruction data reception unit, whereby a prescription waiting time of the user and a time period required for the prescription for the user can be shortened, and additionally a closer and more detailed prescription can be provided by the affiliated facility.

According to the contact lens selection system, it is preferred that the management server further includes a prescription data recording unit for recording a correlation between the data of the contact lenses selected by the contact lens selection unit and the data of the prescription executed by the affiliated facility that received the request from the prescription requesting unit, and the contact lens selection unit selects the one or a plurality of contact lenses after making a correction based on the data recorded by the prescription data recording unit. According to the contact lens selection system, the prescription data recording unit records the data of the contact lenses selected by the contact lens selection unit and data of the contact lens prescribed in the affiliated facility that received the request from the prescription requesting unit. Therefore, the contact lens selection system can determine an error bound for the contact lens selection unit from a difference between the data of the contact lenses selected by the contact lens selection unit and the data of the contact lens prescribed in the affiliated facility that received the request from the prescription requesting unit. Accordingly, the contact lens selection system can improve fitting properties of the selected contact lens, since the contact lens selection unit makes a correction based on such an error.

According to the contact lens selection system, it is preferred that the prescription data recording unit records the data of the contact lenses selected by the contact lens selection unit and the data of the prescription executed by the affiliated facility, in relationship to the user identification data, and the contact lens selection unit makes a correction with respect to each user based on the data recorded by the prescription data recording unit. Accordingly, so far as a user who uses the contact lens selection system more than once is concerned, fitting properties of the contact lenses selected by the contact lens selection unit can be further improved.

According to the contact lens selection system, it is preferred that the management server further includes a delivery assistance unit for executing a delivery procedure to deliver a contact lens corresponding to the data of the contact lens transmitted by the prescription instruction data transmission unit to the affiliated facility that received the request from the prescription requesting unit. Accordingly, a contact lens being likely to be purchased by the user can be delivered to an affiliated facility in advance, and consequently a process of purchase of a contact lens by the user can proceed more smoothly. In addition, according to the contact lens selection system, the affiliated facility does not need to order a necessary contact lens, and therefore an inventory control of contact lenses in the affiliated facility can be facilitated.

According to the contact lens selection system, it is preferred that the management server further includes a use fee settlement unit for executing a settlement procedure for a use fee for the apparatus for optometric self-examination. Accordingly, the user can smoothly proceed with a payment procedure.

According to the contact lens selection system, it is preferred that the management server further includes a system use fee settlement unit for executing a settlement procedure for a system use fee including a use fee for the apparatus for optometric self-examination and a purchase price of the contact lens obtained after the prescription executed in the affiliated facility under assumption of a lump sum payment thereof. Accordingly, the user can proceed with a payment procedure collectively at an appropriate time, and consequently the efficiency of the settlement procedure can be promoted.

Effects of the Invention

As explained in the foregoing, the apparatus for optometric self-examination according to the aspect of the present invention can be readily utilized even by a new user. The apparatus for optometric self-examination, the management server and the contact lens selection system using the same according to the aspects of the present invention can shorten a time period required by an eye care practitioner for prescription, or even if a prescription by an eye care practitioner is absent, enables a contact lens preferable for the user to be easily and reliably selected.

BRIEF DESCRIPTION OF THE DRAWINGS

FIG. 1 is a schematic block diagram illustrating an apparatus for optometric self-examination according to an embodiment of the present invention;

DESCRIPTION OF EMBODIMENTS

Figure 2:
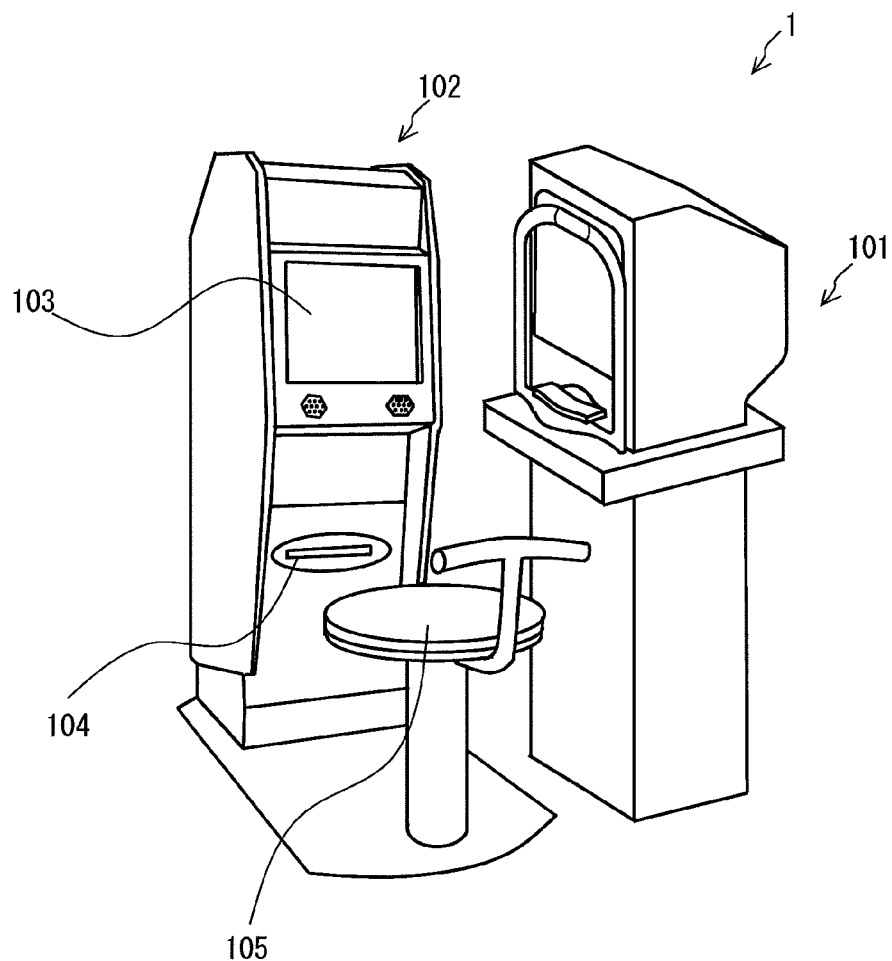
FIG. 2 is a schematic perspective view illustrating the apparatus for optometric self-examination shown in FIG. 1.

Hereinafter, embodiments of the present invention will be described in more detail with references to the drawings, if necessary.

An apparatus for optometric self-examination 1 shown in FIG. 1 includes an optometric data acquisition unit 2, a contact lens data display unit 3, a contact lens selection unit 4, a user selection unit 5, a printing unit 6, and a database 7.

The apparatus for optometric self-examination 1 includes a basic data measurement terminal 101 and a user operation terminal 102, as shown in FIG. 2. The basic data measurement terminal 101 and the user operation terminal 102 are interlinked as a system, and are configured to be able to transmit and receive data therebetween. The basic data measurement terminal 101 includes a corneal shape determination unit, a refractive index measurement unit, and an analysis unit (each not shown in the Figure). The basic data measurement terminal 101 determines/measures a shape of a cornea and a refractive index of the eye of a user by means of the corneal shape determination unit, the refractive index measurement unit and the analysis unit. The user operation terminal 102 includes a touchscreen 103 and a paper ejection unit 104. The apparatus for optometric self-examination 1 is generally installed, for example, inside or outside a contact lens store, an ophthalmic facility, a station, a convenience store, and the like. The apparatus for optometric self-examination 1 is typically installed in a booth (not shown in the Figure), and such a booth prevents an operation of the user and the like from being visually recognized by the people around the user. A chair 105 is configured to be rotatable. The user sits on the chair 105, and gives a predetermined instruction and the like to the apparatus for optometric self-examination 1 through an input from the touchscreen 103. The touchscreen 103 displays information necessary for the user, and also receives the data entered by the user. The paper ejection unit 104 ejects a form on which predetermined data is printed in accordance with the user's instruction. Such an ejection processing is executed by a printer connected to the user operation terminal 102 (not shown in the Figure). The user operation terminal 102 includes a use fee slot (not shown in the Figure) through which the user inserts money for a use fee. The apparatus for optometric self-examination 1 provides the user who paid the predetermined use fee with a service corresponding to the use fee. Moreover, the basic data measurement terminal 101 and the user operation terminal 102 each include a CPU therein. The CPU controls each part in accordance with the user's instruction and the like provided from the touchscreen 103, such that the contents of the instruction are reflected.

The optometric data acquisition unit 2 includes a corneal shape determination unit, a refractive index measurement unit, an analysis unit and a CPU. The optometric data acquisition unit 2 determines at least a part of a shape of a cornea of a user in response to an operation by the user, and acquires optometric data, based on the shape of the cornea. Specifically, when an instruction to acquire the optometric data is conveyed from the user through touching of the touchscreen 103, the optometric data acquisition unit 2 acquires as the optometric data, curvature data at a plurality of points on the surface of the cornea of the user from the corneal shape determination unit. Such curvature data may be obtained through measurements at 3 to 8 points or more in the vicinity of the center of the cornea. In addition, the optometric data acquisition unit 2 measures a transverse corneal diameter of the user via the corneal shape determination unit, and acquires data of the transverse corneal diameter. Furthermore, the optometric data acquisition unit 2 subjectively or objectively measures a refractive index of the eye of the user in response to an operation by the user via the refractive index measurement unit and acquires eye refractive index data.

The contact lens data display unit 3 includes a touchscreen 103 and a CPU. The contact lens data display unit 3 displays a result of selection of a contact lens suited for the optometric data, based on the optometric data acquired by the optometric data acquisition unit 2 and the shape data of contact lenses 8 recorded in the database 7. Specifically, the contact lens data display unit 3 acquires from the database 7 shape data 8 on the one or a plurality of contact lenses selected by the contact lens selection unit 4, and product data of the contact lenses such as a trade name, an item stock number and a price (not shown in the Figure) stored in the database 7, in relationship to the shape data of contact lenses 8, and displays them on the touchscreen 103. Moreover, if the contact lens selection unit 4 has acquired data of the lacrimal fluid layer formed between the surface of the cornea of the user and the back face of the contact lens as described later, the contact lens data display unit 3 displays on the touchscreen 103 a fluorescein pattern representing a shape of the lacrimal fluid layer. Furthermore, if the contact lens selection unit 4 has calculated a refraction value in a state of the contact lens being applied to the eye (over-refraction value), as described later, the contact lens data display unit 3 displays the over-refraction value on the touchscreen 103. In addition, if the contact lens selection unit 4 has simulated visual performances in use of the contact lens, the contact lens data display unit 3 displays a result of the simulation of the visual performances on the touchscreen 103.

The contact lens selection unit 4 includes a CPU. The contact lens selection unit 4 selects one or a plurality of contact lenses suited for the optometric data, based on the optometric data acquired by the optometric data acquisition unit 2 and the shape data of contact lenses 8 stored in the database 7. Specifically, the contact lens selection unit 4 first extracts the maximum value and the minimum value among the curvature data at a plurality of points on the surface of the cornea of the user acquired by the optometric data acquisition unit 2 and calculates an average value from the maximum value and the minimum value. Meanwhile, an empirical parameter defined with respect to each contact lens is recorded in the database 7 as the shape data of contact lenses 8. The contact lens selection unit 4 selects a base curve of a contact lens suitable for the user by multiplying the average value of the maximum value and the minimum value among the curvature data by the empirical parameter of the plurality of contact lenses recorded in the database 7. According to the apparatus for optometric self-examination 1, the contact lens selection unit 4 can select a contact lens based on the average value of the curvature data at a plurality of points on the surface of the cornea of the user. Therefore, according to the apparatus for optometric self-examination 1, a contact lens suitable for the user can be easily and rapidly selected by obtaining the curvature data at a plurality of points on the surface of the cornea of the user. Moreover, the contact lens selection unit 4 may select a contact lens after making a correction based on a value (correction value) obtained by subtracting the minimum value from the maximum value among the curvature data at the plurality of points acquired as the optometric data. Such a method of selection of a contact lens is exemplified by a method including: calculating an average value from the maximum value and the minimum value among the curvature data at the plurality of points on the surface of the cornea of the user; multiplying the average value by the empirical parameter defined with respect to each contact lens; and thereafter adding the correction value. When a correction is thus made based on the value obtained by subtracting the minimum value from the maximum value among the curvature data at the plurality of points on the surface of the cornea of the user, a contact lens can be selected in light of the roughness of the cornea surface of the user, and the like, and fitting properties of the selected contact lens to the user can be improved. It is to be noted that the term "empirical parameter" as referred to herein is derived by analyzing a number obtained from clinical experiences (a numerical value obtained by deriving a certain formula from clinical experiences and executing a prescription based on the formula).

Moreover, the contact lens selection unit 4 determines a dioptric power of the contact lenses such as a spherical dioptric power and an astigmatic dioptric power based on the eye refractive index data acquired by the optometric data acquisition unit 2. According to the optometry apparatus 1, the contact lens selection unit 4 determines a dioptric power of the contact lenses based on the eye refractive index data, whereby a dioptric power of a contact lens suitable for the user can be easily and rapidly determined. Moreover, the contact lens selection unit 4 may be configured to calculate spatial data of a space formed between the surface of the cornea of the user and the back face of the contact lens from the curvature data at a plurality of points on the surface of the cornea of the user and as the shape data of contact lenses 8 the data of a base curve of contact lenses recorded in the database 7, and then acquire the spatial data as data of a lacrimal fluid layer formed between the surface of the cornea of the user and the back face of the contact lens to determine the dioptric power of the contact lenses in light of the shape of the lacrimal fluid layer. Such a method for determining a dioptric power of the contact lenses is exemplified by a method including: assuming that an air layer, a contact lens layer, a lacrimal fluid layer and the cornea respectively constitute a lens group; simulating a total aberration in use of the contact lens; and determining a spherical dioptric power and an astigmatic dioptric power of a contact lens suitable for the user based on a result of such a simulation. According to the optometry apparatus 1, accuracy of the dioptric power of the contact lenses selected by the contact lens selection unit 4 can be further improved by determining the dioptric power of the contact lenses in light of the shape of the lacrimal fluid layer as described above.

Furthermore, the contact lens selection unit 4 may calculate a refraction value in a state of the contact lens being applied to the eye by the user (over-refraction value) based on the optometric data, the spatial data and the shape data of the contact lens selected. In addition, the contact lens selection unit 4 may simulate visual performances in use of the contact lens based on the over-refraction value. Such a simulation can be performed with a well-known ophthalmological optics-based simulation unit.

Moreover, the contact lens selection unit 4 determines a diameter of the contact lens based on the data of the transverse corneal diameter of the user acquired by the optometric data acquisition unit 2. For example, in the case of hard contact lenses, the contact lens selection unit 4 defines as the diameter of the contact lens a value obtained by subtracting about 1.5 to 2.5 mm from the value of the data of the transverse corneal diameter acquired by the optometric data acquisition unit 2. The apparatus for optometric self-examination 1 thus determines a diameter of the thus determines a diameter of the contact lens based on the data of the transverse corneal diameter acquired by the optometric data acquisition unit 2, whereby the diameter of a contact lens suitable for the user can be easily and rapidly selected.

It is to be noted that, the database 7 may store, as the shape data of contact lenses 8, a shape of a bevel of a plurality of contact lenses, and the contact lens selection unit 4 may select a contact lens in light of the shape of the bevel.

The user selection unit 5 includes a touchscreen 103 and a CPU. The user selection unit 5 permits the user to select any contact lens from among the plurality of contact lenses the data of which are displayed by the contact lens data display unit 3. Specifically, the user selection unit 5 first allows the contact lens data display unit 3 to display data of the plurality of contact lenses that may be selected by the user. The contact lens data display unit 3 displays such data of the contact lenses on the touchscreen 103. The user selection unit 5 receives from the user via the touchscreen 103 an input to the effect that the user has selected a certain contact lens. It is to be noted that the user may select either one contact lens, or a plurality of contact lenses.

The printing unit 6 includes a printer and a CPU. The printing unit 6 prints the optometric data acquired by the optometric data acquisition unit 2 and the data of the contact lenses selected by the contact lens selection unit 4. When the printing unit 6 receives from the user via the touchscreen 103 an instruction to print the optometric data acquired by the optometric data acquisition unit 2 and the data of the contact lenses selected by the contact lens selection unit 4, the printing unit 6 prints these data on a predetermined form. The form including the data printed by the printing unit 6 is ejected from the paper ejection unit 104. It is to be noted that the printing unit 6 does not necessarily have to print both the optometric data and the data of the contact lens, and may print only the optometric data or only the data of the contact lenses according to the user's choice, the content of the service or the like. Furthermore, the printing unit 6 may be configured to print the data of the contact lenses selected by the user selection unit 5. Moreover, the printing unit 6 may include a photographic printing unit.

The database 7 contains shape data 8 of contact lenses stored by recording shape data of a plurality of contact lenses such as a diameter, a base curve, a dioptric power, a central thickness, an empirical parameter, and a shape of a bevel of the contact lenses. Shape data of various contact lenses 8 such as soft contact lenses and hard contact lenses are recorded as the shape data of contact lenses 8. Moreover, product data representing product information of the contact lenses such as a trade name, an item stock number and a price of the contact lenses corresponding to the shape data of contact lenses 8 are recorded in the database 7 in relationship to the shape data of contact lenses 8.

Figure 3:
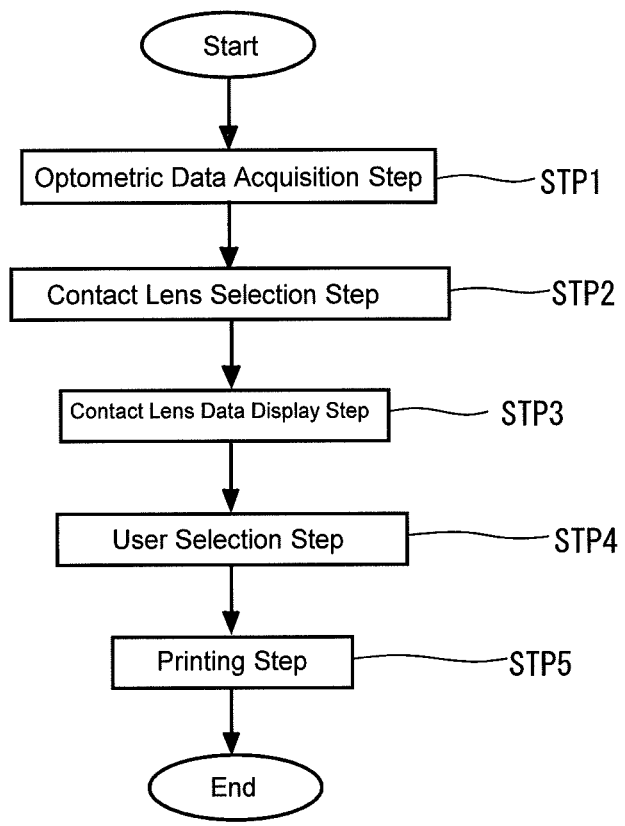
FIG. 3 is a flowchart illustrating an operational procedure of the apparatus for optometric self-examination shown in FIG. 1.

Referring to FIG. 3, an operational procedure of the apparatus for optometric self-examination 1 will be explained.

An optometric data acquisition step (STP 1) is a step of determining at least a part of a shape of a cornea of a user in response to an operation by the user and acquiring optometric data, based on the shape of the cornea. STP 1 is executed by the optometric data acquisition unit 2. When the optometric data acquisition unit 2 receives from the user via the touchscreen 103 an instruction to acquire the optometric data, the optometric data acquisition unit 2 acquires as the optometric data, curvature data at a plurality of points on the surface of the cornea of the user from the corneal shape determination unit. Moreover, the optometric data acquisition unit 2 measures a transverse corneal diameter of the user with the corneal shape determination unit and acquires data of the transverse corneal diameter. Furthermore, the optometric data acquisition unit 2 subjectively or objectively measures a refractive index of the eye of the user in response to an operation by the user via the refractive index measurement unit and acquires eye refractive index data.

A contact lens selection step (STP 2) is a step of selecting one or a plurality of contact lenses suited for the optometric data, based on the optometric data acquired in STP 1 and the shape data of contact lenses 8 stored in the database 7. STP 2 is executed by the contact lens selection unit 4. In STP 2, the contact lens selection unit 4 first extracts the maximum value and the minimum value from among the curvature data at a plurality of points on the surface of the cornea of the user acquired in STP 1 and calculates an average value from the maximum value and the minimum value. On the other hand, an empirical parameter defined with respect to each contact lens is recorded in the database 7 as the shape data of contact lenses 8. The contact lens selection unit 4 selects a base curve of a contact lens suitable for the user by multiplying the average value of the maximum value and the minimum value among the curvature data by the empirical parameter of a plurality of contact lenses recorded in the database 7. Alternatively, the contact lens selection unit 4 may select a contact lens after making a correction based on a value (correction value) obtained by subtracting the minimum value from the maximum value among the curvature data at the plurality of points acquired as the optometric data. Such a method of selection of a contact lens is exemplified by a method including: calculating an average value from the maximum value and the minimum value among the curvature data at the plurality of points on the surface of the cornea of the user; multiplying the average value by the empirical parameter defined with respect to each contact lens; and thereafter adding the correction value.

Moreover, the contact lens selection unit 4 determines a dioptric power of the contact lenses such as a spherical dioptric power and an astigmatic dioptric power based on the eye refractive index data acquired by the optometric data acquisition unit 2. In the determination, the contact lens selection unit 4 may calculate spatial data of a space formed between the surface of the cornea of the user and the back face of the contact lens from the curvature data at a plurality of points on the surface of the cornea of the user and as the shape data of contact lenses 8 the data of a base curve of contact lenses recorded in the database 7, and then acquire the spatial data as data of a lacrimal fluid layer formed between the surface of the cornea of the user and the back face of the contact lens to determine the dioptric power of the contact lenses in light of the shape of the lacrimal fluid layer. Such a method for determining a dioptric power of the contact lenses is exemplified by a method including: assuming that an air layer, a contact lens layer, a lacrimal fluid layer and the cornea respectively constitute a lens group; simulating a total aberration in use of the contact lens; and determining a spherical dioptric power and an astigmatic dioptric power of a contact lens suitable for the user based on a result of such a simulation.

Furthermore, the contact lens selection unit 4 may calculate a refraction value in a state of the contact lens being applied to the eye by the user (over-refraction value) based on the optometric data, the spatial data and the shape data of the contact lens selected. In addition, the contact lens selection unit 4 may simulate visual performances in use of the contact lens based on the over-refraction value.

Moreover, the contact lens selection unit 4 determines a diameter of the contact lens based on the data of the transverse corneal diameter of the user acquired by the optometric data acquisition unit 2. For example, in the case of hard contact lenses, the contact lens selection unit 4 defines as the diameter of the contact lens a value obtained by subtracting about 1.5 to 2.5 mm from the value of the data of the transverse corneal diameter acquired by the optometric data acquisition unit 2.

It is to be noted that the database 7 may store, as the shape data of contact lenses 8, a shape of a bevel of a plurality of contact lenses, and the contact lens selection unit 4 may select a contact lens in light of the shape of the bevel.

A contact lens data display step (STP 3) is a step of displaying the data of the contact lenses selected in STP 2. STP 3 is executed by the contact lens data display unit 3. In STP 3, the contact lens data display unit 3 displays on the touchscreen 103, in regard to the one or a plurality of contact lenses selected in STP 2, shape data 8 of these contact lenses and product data stored in the database 7 in relationship to the shape data of contact lenses 8. Moreover, if the data of the lacrimal fluid layer formed between the surface of the cornea of the user and the back face of the contact lens has been acquired in STP 2, the contact lens data display unit 3 displays on the touchscreen 103 a fluorescein pattern representing the shape of the lacrimal fluid layer in STP 3. Furthermore, if a refraction value in a state of the contact lens being applied to the eye by the user (over-refraction value) has been calculated in STP 2, the contact lens data display unit 3 displays the over-refraction value on the touchscreen 103 in STP 3. In addition, if visual performances in use of the contact lens have been simulated in STP 2, the contact lens data display unit 3 displays a result of the simulation of the visual performances on the touchscreen 103 in STP 3.

A user selection step (STP 4) is a step of allowing the user to select any contact lens from among the plurality of contact lenses displayed in STP 3. STP 4 is executed by the user selection unit 5. The user selection unit 5 first permits the contact lens data display unit 3 to display the data of a plurality of contact lenses that may be selected by the user. The contact lens data display unit 3 displays the data of such contact lenses on the touchscreen 103. The user selection unit 5 receives from the user via the touchscreen 103 an input to the effect that the user has selected a certain contact lens. It is to be noted that the number of the contact lenses entered by the user into the user selection unit 5 may be either one, or more than one. Moreover, if one contact lens is displayed in STP 3, STP 4 may be omitted.

A printing step (STP 5) is a step of printing the optometric data acquired in STP 1 and the data of the contact lenses selected in STP 2. STP 5 is executed by the printing unit 6. When the printing unit 6 receives from the user via the touchscreen 103 an instruction to print the optometric data acquired in STP 1 and the data of the contact lenses selected in STP 2, the printing unit 6 prints these data on a predetermined form. The form including the data printed by the printing unit 6 is ejected from the paper ejection unit 104. It is to be noted that in STP 5, it is not necessary to print both the optometric data and the data of the contact lenses, and only the optometric data or only the data of the contact lenses may be printed according to the user's choice, the content of the service or the like. Furthermore, in STP 5, the data of the contact lenses selected by the user selection unit 5 may be printed.

According to the apparatus for optometric self-examination 1, the optometric data acquisition unit 2 may acquire optometric data in response to an operation by the user, and the contact lens data display unit 3 may display data of the a contact lens suited for the optometric data. Accordingly, the apparatus for optometric self-examination 1 is readily available to even a new user through the user's own operation, and the user can find a contact lens suitable for the user. Moreover, according to the apparatus for optometric self-examination 1, if an eye care practitioner uses optometric data and the data of the contact lenses displayed by the contact lens data display unit 3, a time period required by the eye care practitioner for prescription can be shortened.

The apparatus for optometric self-examination 1 can select a contact lens suitable for the user via the contact lens selection unit 4. According to the apparatus for optometric self-examination 1, since the contact lens selection unit 4 selects one or a plurality of contact lenses suited for the user based on the shape data 8 of a plurality of contact lenses stored in the database 7, lack of an eye care practitioner's skill can be favorably compensated for by storing in the database 7 shape data of various contact lenses such as soft contact lenses and hard contact lenses, and a contact lens suitable for the user can be provided. Briefly, in recent years, soft contact lenses, and disposable contact lenses in particular, become widely used, and along with such a situation, a decrease of an opportunity of prescribing a hard contact lens is pronounced, and a reduction of a technical level of eye care practitioners caused by this decrease is observed. To address this circumstance, the apparatus for optometric self-examination 1 can store in the database 7 the shape data of various contact lenses such as soft contact lenses and hard contact lenses, and enables a hard contact lens suitable for the user to be selected based on such data of the contact lenses. Therefore, according to the apparatus for optometric self-examination 1, even an eye care practitioner who is inexperienced in prescription of a hard contact lens can prescribe a hard contact lens suitable for the user based on the selection carried out by the contact lens selection unit 4.

According to the apparatus for optometric self-examination 1, since the contact lens data display unit 3 can display a fluorescein pattern representing the shape of the lacrimal fluid layer, the user can ascertain the fluorescein pattern without using a trial lens. Moreover, according to such a constitution, the user can visually ascertain fitting properties of the contact lens, and consequently a comfort level of the user can be enhanced.

According to the apparatus for optometric self-examination 1, since the contact lens selection unit 4 can calculate a refraction value in a state of the contact lens being applied to the eye (over-refraction value) and the contact lens data display unit 3 can display the over-refraction value, validity of the contact lenses selected by the contact lens selection unit 4 can be displayed to the user, and consequently a comfort level of the user can be enhanced.

According to the apparatus for optometric self-examination 1, since the contact lens selection unit 4 simulates visual performances in use of the contact lens based on the over-refraction value, and the contact lens data display unit 3 can display a result of the simulation of the visual performances, validity of the contact lenses selected by the contact lens selection unit 4 can be displayed to the user, and a comfort level of the user can be further enhanced.

Since the apparatus for optometric self-examination 1 includes the user selection unit 5 for allowing the user to select any contact lens from among a plurality of contact lenses displayed by the contact lens data display unit 3, a contact lens suitable for the user and preferred by the user can be easily selected.

Since the apparatus for optometric self-examination 1 includes the printing unit 6, the user can easily acquire the user's own optometric data and the data of a contact lens suitable for the user and keep these data on hand. Therefore, according to the apparatus for optometric self-examination 1, the user can ascertain the user's own optometric data and the data of a contact lens suitable for the user any time. Furthermore, according to the apparatus for optometric self-examination 1, the user can visit a contact lens store and the like with these data held in the user's hand and purchase the desired contact lens, or alternatively visit an eye care practitioner and the like with these data held in the user's hand and receive a closer and more detailed prescription.

Figure 4:
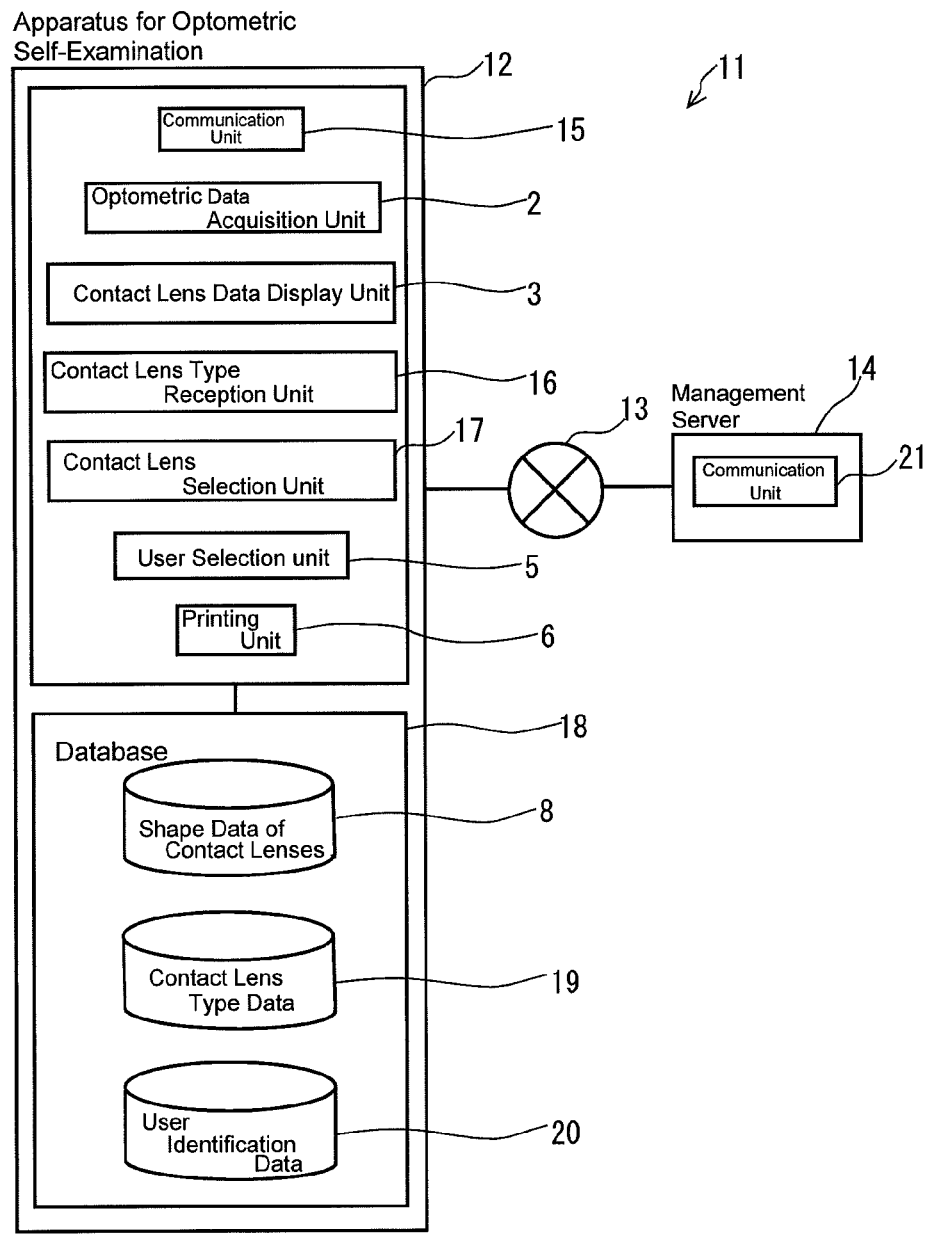
FIG. 4 is a schematic block diagram illustrating a contact lens selection system according to another embodiment of the present invention.

The contact lens selection system 11 shown in FIG. 4 includes an apparatus for optometric self-examination 12, a network 13, and a management server 14. The contact lens selection system 11 practically includes the apparatus for optometric self-examination 12 in a plurality of number. However, in FIG. 4, only one apparatus for optometric self-examination 12 is shown in order to avoid complication. Moreover, in the following description, the components identical to those of the apparatus for optometric self-examination 1 shown in FIG. 1 are designated using the same number as in FIG. 1 and explanation thereof will be omitted accordingly.

The apparatus for optometric self-examination 12 includes a communication unit 15, an optometric data acquisition unit 2, a contact lens data display unit 3, a contact lens type reception unit 16, a contact lens selection unit 17, a user selection unit 5, a printing unit 6, and a database 18. The apparatus for optometric self-examination 12 also includes a basic data measurement terminal 101 and a user operation terminal 102, similarly to the apparatus for optometric self-examination 1 shown in FIG. 2.

The communication unit 15 controls network-communication between the apparatus for optometric self-examination 12 and an external apparatus such as the management server 14. The communication unit 15 transmits, as prescription-related data, the optometric data acquired by the optometric data acquisition unit 2 and the data of the contact lenses selected by the contact lens selection unit 4 to the management server 14 or other external apparatuses in relationship to the user identification data 20 of the user stored in the database 18 (prescription-related data transmission unit). Moreover, the communication unit 15 transmits the data of the contact lenses selected by the user selection unit 5 to the management server 14 in relationship to the user identification data 20 of the user stored in the database 18.

The contact lens type reception unit 16 includes a touchscreen 103 and a CPU. The contact lens type reception unit 16 receives an input of contact lens type data desired by the user. Specifically, the contact lens type reception unit 16 receives, via the touchscreen 103, the user's demand for contact lens types including the type of general contact lenses for vision correction such as a hard type and a soft type; application mode such as daily wear, extended-wear and occasional use; service life such as disposable, planned replacement and long-term use; as well as intended usages such as bifocal and for keratoconus and for fashion. The contact lens type reception unit 16 may receive the user's demand by displaying these contact lens types on the touchscreen 103 and allowing the user to select a contact lens type, or may receive the user's demand by receiving a direct input from the user via the touchscreen 103.

The contact lens selection unit 17 includes a CPU. The contact lens selection unit 17 selects one or a plurality of contact lenses suited for the optometric data, based on the optometric data acquired by the optometric data acquisition unit 2 and the shape data of contact lenses 8 stored in the database 18. Moreover, the contact lens selection unit 17 selects a contact lens that matches the contact lens type received by the contact lens type reception unit 16. Specifically, the contact lens type data 19 representing the contact lens type as described above are stored in the database 18 in relationship to the shape data of contact lenses 8. More specifically, the shape data of contact lenses 8 are stored in the database 18 in relationship to the contact lens type data 19, such that each type of the contact lenses is clarified, the data of which have been recorded in the shape data of contact lenses 8. The contact lens selection unit 17 selects a contact lens suitable for the user among the contact lenses that match the contact lens type received by the contact lens type reception unit 16, with reference to the contact lens type data 19 and the shape data of contact lenses 8. It is to be noted that the method of selection of a base curve, a dioptric power, a diameter and the like of the contact lens executed by the contact lens selection unit 17 is similar to that in the contact lens selection unit 4.

The database 18 contains the shape data of contact lenses 8, the contact lens type data 19 and the user identification data 20. A user ID code to uniquely identify each user, as well as the user's full name, date of birth, address, past history, account number and the like corresponding to the user ID code are recorded as the user identification data 20 in relationship to each other. The user's full name, date of birth, address, past history, account number and the like are recorded in relationship to the user ID code arbitrarily issued with respect to the user, as a result of the entry thereof by the user via the touchscreen 103, and the like, at the time of his/her first use of the apparatus for optometric self-examination 12. Moreover, the optometric data and the contact lenses data acquired by the optometric data acquisition unit 2, the contact lens type reception unit 16, the contact lens selection unit 17 and the user selection unit 5 are recorded in the database 18 in relationship to the user identification data 20 of the user corresponding to these data. Although the user identification data transmitted by the communication unit 15 are typically exemplified by the user ID code, the data recorded in relationship to the user ID code may also be appropriately transmitted if necessary.

The network 13 is typically an Internet. The network 13 is constructed to be able to connect the apparatus for optometric self-examination 12 with the management server 14.

The management server 14 includes a communication unit 21. The management server 14 may be constituted of one or a plurality of computers. Moreover, the management server 14 may include a certain input apparatus, and the like. The communication unit 21 controls network-communication between the management server 14 and an external apparatus such as the apparatus for optometric self-examination 12. The communication unit 21 receives the prescription-related data transmitted by the prescription-related data transmission unit (prescription-related data reception unit). In addition, the communication unit 21 receives the data of the contact lenses selected by the user selection unit 5 and the user identification data 20 of the user from the apparatus for optometric self-examination 12.

The apparatus for optometric self-examination 12 according to the embodiment of the present invention can select a contact lens in accordance with preference of the user, since the contact lens selection unit 17 selects a contact lens that matches the contact lens type received by the contact lens type reception unit 16.

According to the apparatus for optometric self-examination 12, the prescription-related data transmission unit is capable of transmitting via a network the prescription-related data. Therefore, according to the apparatus for optometric self-examination 12, an eye care practitioner who prescribes for the user, and the like can receive on a predetermined apparatus the prescription-related data transmitted by the prescription-related data transmission unit and thereafter perform a prescription using the prescription-related data. Therefore, according to the apparatus for optometric self-examination 12, a time period required by an eye care practitioner for prescription can be shortened, and additionally more detailed prescription may be provided by the eye care practitioner. Moreover, according to the apparatus for optometric self-examination 12, a contact lens suitable for the user can be selected or obtained without a need of prescription by an eye care practitioner based on the prescription-related data transmitted by the prescription-related data transmission unit. Furthermore, if the apparatus for optometric self-examination 12 is configured to transmit the prescription-related data to a personal computer possessed by the user and the like, the apparatus for optometric self-examination 12 enables the user to readily conduct viewing, managing and the like by him/herself the optometric data and the data of the contact lenses as well as changes of the optometric data and the data of the contact lens and the like, and consequently can enhance the user's awareness of information on the user's own eye.

Figure 5:
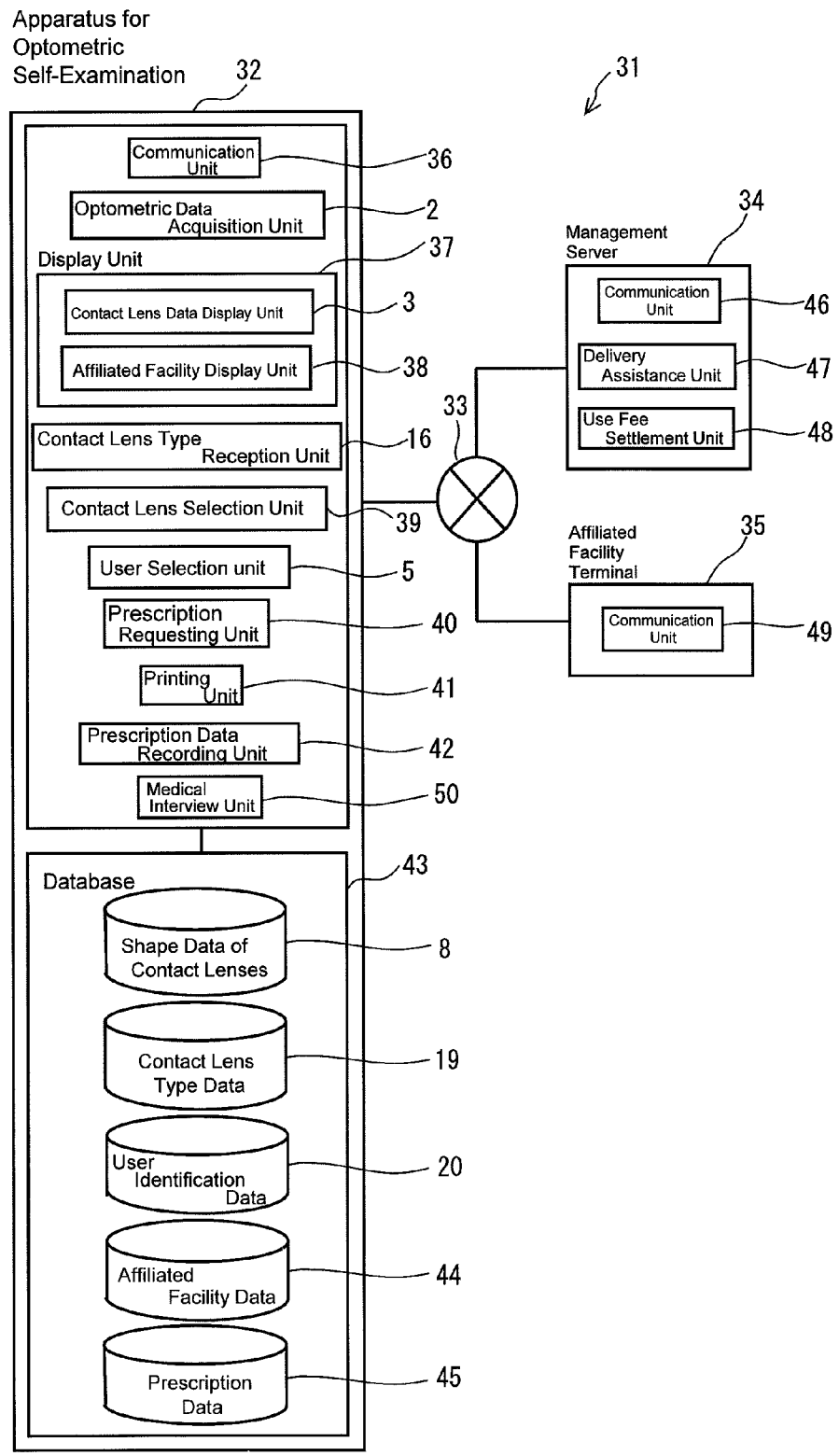
FIG. 5 is a schematic block diagram illustrating a contact lens selection system according to an embodiment different from the contact lens selection system shown in FIG. 4.

The contact lens selection system 31 shown in FIG. 5 includes an apparatus for optometric self-examination 32, a network 33, a management server 34 and an affiliated facility terminal 35. The contact lens selection system 31 practically includes the apparatus for optometric self-examination 32 and the affiliated facility terminal 35 in a plurality of number. However, in FIG. 5, only one apparatus for optometric self-examination 32 and only one affiliated facility terminal 35 are shown in order to avoid complication. Moreover, in the following description, the components identical to those of the apparatus for optometric self-examination 1 shown in FIG. 1 and the contact lens selection system 11 shown in FIG. 4 are designated using the same number as in FIGS. 1 and 4 and explanation thereof will be omitted accordingly.

The apparatus for optometric self-examination 32 includes a communication unit 36, an optometric data acquisition unit 2, a display unit 37, a contact lens type reception unit 16, a contact lens selection unit 39, a user selection unit 5, a prescription requesting unit 40, a printing unit 41, a prescription data recording unit 42, a medical interview unit 50, and a database 43. The apparatus for optometric self-examination 32 includes a basic data measurement terminal 101 and a user operation terminal 102 similarly to the apparatus for optometric self-examination 1 shown in FIG. 2.

The communication unit 36 controls network-communication among the apparatus for optometric self-examination 32, the management server 34 and an external apparatus such as the affiliated facility terminal 35. The communication unit 36 transmits, as prescription-related data, the optometric data acquired by the optometric data acquisition unit 2 and data of the contact lenses selected by the contact lens selection unit 39 to the management server 34 or other external apparatuses in relationship to the user identification data 20 of the user stored in the database 43 (prescription-related data transmission unit). Moreover, the communication unit 36 transmits the data of the contact lenses selected by the user selection unit 5 to the management server 34 in relationship to the user identification data 20 of the user stored in the database 43 (second contact lens data transmission unit).

The display unit 37 includes a contact lens data display unit 3 and an affiliated facility display unit 38. The display unit 37 includes a touchscreen 103 and a CPU. The affiliated facility display unit 38 displays data of a plurality of affiliated facilities capable of prescribing a contact lens. Specifically, when an instruction to display affiliated facilities capable of prescribing a contact lens is conveyed from the user to the affiliated facility display unit 38 through touching of the touchscreen 103, the affiliated facility display unit 38 displays data of the affiliated facility associated with the affiliated facility terminal 35 on the touchscreen 103, based on affiliated facility data 44 stored in the database 43 as described later.

The contact lens selection unit 39 includes a CPU. The contact lens selection unit 39 selects a contact lens that matches the contact lens type received by the contact lens type reception unit 16. A process in which the contact lens selection unit 39 selects a contact lens that matches the contact lens type received by the contact lens type reception unit 16 is identical to the process involving the contact lens selection unit 17. Moreover, the contact lens selection unit 39 selects a contact lens after making a correction based on the data recorded by the prescription data recording unit 42. Specifically, the contact lens selection unit 39 first extracts the maximum value and the minimum value among the curvature data at the plurality of points on the surface of the cornea of the user acquired by the optometric data acquisition unit 2 and calculates an average value from the maximum value and the minimum value. The contact lens selection unit 39 selects (primarily selects) a base curve of a contact lens suitable for the user by multiplying the average value of the maximum value and the minimum value among the curvature data by the empirical parameter of a plurality of contact lenses recorded as the shape data of contact lenses 8. It is to be noted that the contact lens selection unit 39 may select a base curve after making a correction based on a value (correction value) obtained by subtracting the minimum value from the maximum value among the curvature data at the plurality of points acquired as the optometric data. Such a method of selection of a base curve is exemplified by a method including: calculating an average value from the maximum value and the minimum value among the curvature data at the plurality of points on the surface of the cornea of the user; multiplying the average value by an empirical parameter defined with respect to each contact lens; and thereafter adding the correction value.

Moreover, the contact lens selection unit 39 determines a dioptric power of the contact lenses such as a spherical dioptric power and an astigmatic dioptric power based on the eye refractive index data acquired by the optometric data acquisition unit 2. Alternatively, the contact lens selection unit 39 may calculate spatial data of a space formed between the surface of the cornea of the user and the back face of the contact lens from the curvature data at a plurality of points on the surface of the cornea of the user and as the shape data of contact lenses 8 the data of a base curve of contact lenses recorded in the database 43, and then acquire the spatial data as data of a lacrimal fluid layer formed between the surface of the cornea of the user and the back face of the contact lens to determine the dioptric power of the contact lenses in light of the shape of the lacrimal fluid layer. Such a method for determining a dioptric power of the contact lenses is exemplified by a method including: assuming that an air layer, a contact lens layer, a lacrimal fluid layer and the cornea respectively constitute a lens group; simulating a total aberration in use of the contact lens; and determining a spherical dioptric power and an astigmatic dioptric power of a contact lens suitable for the user based on a result of such a simulation.

Furthermore, the contact lens selection unit 39 may calculate a refraction value in a state of the contact lens being applied to the eye by the user (over-refraction value) based on the optometric data, the spatial data and the shape data of the contact lens selected. In addition, the contact lens selection unit 39 may simulate visual performances in use of the contact lens based on the over-refraction value.

Moreover, the contact lens selection unit 39 determines a diameter of the contact lens based on the data of the transverse corneal diameter of the user acquired by the optometric data acquisition unit 2. For example, in the case of hard contact lenses, the contact lens selection unit 39 defines as the diameter of the contact lens a value obtained by subtracting about 1.5 to 2.5 mm from the value of the data of the transverse corneal diameter acquired by the optometric data acquisition unit 2.

It is to be noted that the database 43 may store, as the shape data of contact lenses 8, a shape of a bevel of a plurality of contact lenses, and the contact lens selection unit 39 may select a contact lens in light of the shape of the bevel.

Subsequently, the contact lens selection unit 39 calculates, based on the prescription data 45, which is an accumulation of results of prescriptions executed in the past, an average of errors between values of the base curve of the primarily selected contact lenses and values of the base curve of the contact lenses actually and finally decided to be prescribed in the affiliated facility. Such an average of the errors can be determined by calculating an average of errors 45a recorded in prescription data 45. The contact lens selection unit 39 corrects the value of the base curve of the primarily selected contact lenses by such an average value of the errors, and selects (finally selects) one or a plurality of final contact lenses suited for the user. It is to be noted that such a correction may be made to the dioptric power, the diameter and the like of the contact lens in addition to the base curve of the contact lens.

The prescription requesting unit 40 includes a touchscreen 103 and a CPU. The prescription requesting unit 40 permits the affiliated facility display unit 38 to display data of a plurality of affiliated facilities capable of prescribing a contact lens. The affiliated facility display unit 38 displays the data of the affiliated facilities on the touchscreen 103. When the prescription requesting unit 40 receives from the user via the touchscreen 103 an input to the effect that the user has selected a certain affiliated facility, the prescription requesting unit 40 displays prescription available dates of the affiliated facility on the touchscreen 103. The prescription requesting unit 40 receives the date selected by the user, as the date appointed for prescription for the user, from among the prescription available dates displayed on the touchscreen 103. It is to be noted that data indicating prescription availability of the affiliated facility and the like may be stored in the apparatus for optometric self-examination 32, or in other apparatus such as the management server 34. The date selected by the prescription requesting unit 40 is at least communicated to the management server 34 and the affiliated facility terminal 35 requested for prescription, or uploaded such that the date can be freely viewed from the management server 34 and the affiliated facility terminal 35 requested for prescription.

The printing unit 41 includes a printer and a CPU. The printing unit 41 prints the optometric data acquired by the optometric data acquisition unit 2 and the data of the contact lenses selected by the contact lens selection unit 39. When the printing unit 41 receives from the user via the touchscreen 103 an instruction to print the optometric data acquired by the optometric data acquisition unit 2 and the data of the contact lenses selected by the contact lens selection unit 39, the printing unit 41 prints these data on a predetermined form. The form including the data printed by the printing unit 41 is ejected from the paper ejection unit 104. Moreover, the printing unit 41 may print the data of the contact lenses selected by the user selection unit 5, or print the prescription requesting date appointed from the prescription requesting unit 40. The printing unit 41 may include a photographic printing unit.

The prescription data recording unit 42 includes a CPU. The prescription data recording unit 42 records the correlation between the data of the contact lenses selected by the contact lens selection unit 39 and the data of the prescription executed by the affiliated facility that received the request from the prescription requesting unit 40. Specifically, the prescription data recording unit 42 first records in the database 43 the value of the base curve of the contact lenses primarily selected by the contact lens selection unit 39 (primary selection value) in relationship to the user ID code of the user and the optometry apparatus ID code held by the apparatus for optometric self-examination 32. Next, the prescription data recording unit 42 receives from the affiliated facility terminal 35 a value of a base curve of the contact lens decided to be prescribed in the affiliated facility that received the request from the prescription requesting unit 40 (prescription decision value) and the affiliated facility ID code of the affiliated facility, and records them in the database 43 in relationship to the user ID code, the optometry apparatus ID code and the primary selection value recorded first. These data, which are recorded by the prescription data recording unit 42, are stored in the database 43 as the prescription data 45.

The medical interview unit 50 includes a touchscreen 103 and a CPU. The medical interview unit 50 simplifies a process of purchasing a contact lens by a user who has utilized the contact lens selection system 31 within a predetermined period of time and has purchased or been prescribed with a contact lens. Specifically, the medical interview unit 50 displays the medical interview data via the touchscreen 103 to the user who has utilized the contact lens selection system 31 within a predetermined period of time and has purchased or been prescribed with a contact lens. As the medical interview data, the medical interview data stored in the database 43 in advance (not shown in the Figure) or the medical interview data transmitted from the management server 34 (not shown in the Figure) are employed. The medical interview unit 50 receives a reply to the medical interview from the user via the touchscreen 103. If the reply of the user meets prerequisites, the medical interview unit 50 transmits the user ID code of the user to the management server 34 and the data of such contact lens prescribed for the user last time in relationship to each other. It is to be noted that the user ID code and the data of the contact lenses received by the management server 34 are sent to a delivery assistance unit 47.

The database 43 contains shape data of contact lenses 8, contact lens type data 19, user identification data 20, affiliated facility data 44, and prescription data 45.

As the affiliated facility data 44, an affiliated facility ID code to uniquely identify each affiliated facility, an affiliated facility name corresponding to the affiliated facility ID code, an address, contact information, an eye care practitioner who belongs to the affiliated facility, a fee structure including a charge of a contact lens, an account number and the like are recorded in association.

Figure 6:
FIG. 6 is a diagram illustrating an example of prescription data in the contact lens selection system shown in FIG. 5.

As the prescription data 45, a correlation between the data of the contact lenses selected (primarily selected) by the contact lens selection unit 39 and the data of the prescription executed by the affiliated facility that received the request from the prescription requesting unit 40 is recorded. Specifically, a user ID code of a specific user; an optometry apparatus ID code to identify the apparatus for optometric self-examination 32 used by the user; an affiliated facility ID code to identify the affiliated facility that received the appointment from the user via the prescription requesting unit 40; a value of the base curve of the contact lenses primarily selected by the contact lens selection unit 39 of the apparatus for optometric self-examination 32 (primary selection value); a value of a base curve of the contact lens decided to be prescribed in the affiliated facility that received the request from the prescription requesting unit 40 (prescription decision value); and an error 45a between the primary selection value and the prescription decision value are stored line-by-line in this order in the prescription data 45, as shown in FIG. 6. It is to be noted that the prescription data 45 may contain the dioptric power, the diameter and the like of the contact lens in addition to the base curve of the contact lens.

The network 33 is typically an Internet. The network 33 is constructed to be able to connect the apparatus for optometric self-examination 32, the management server 34 and the affiliated facility terminal 35.

The management server 34 includes a communication unit 46, a delivery assistance unit 47, and a use fee settlement unit 48. The management server 34 may be constituted of one or a plurality of computers. Moreover, the management server 34 may include a certain input apparatus, and the like.

The communication unit 46 controls network-communication among the management server 34, the apparatus for optometric self-examination 32 and an external apparatus such as the affiliated facility terminal 35. The communication unit 46 receives the prescription-related data transmitted via the prescription-related data transmission unit from the apparatus for optometric self-examination 32 (prescription-related data reception unit). Moreover, the communication unit 46 transmits prescription instruction data produced based on the prescription-related data received via the prescription-related data reception unit to an affiliated facility terminal 35 in an affiliated facility in which a prescription is executed and the like (prescription instruction data transmission unit). The communication unit 46 receives the data of the contact lenses transmitted by the second contact lens data transmission unit and the user identification data (second contact lens data reception unit).

The delivery assistance unit 47 includes a CPU. The delivery assistance unit 47 executes a delivery procedure to deliver a contact lens corresponding to the data of the contact lenses transmitted by the prescription instruction data transmission unit to the affiliated facility that received the request from the prescription requesting unit 40. Specifically, the delivery assistance unit 47 first checks an inventory of the contact lenses managed by the management server 34 (the inventory data of the contact lenses are not shown in the Figure) and hence stocks of the contact lenses recommended in the prescription instruction transmitted by the prescription instruction data transmission unit. Next, if the contact lens recommended in the prescription instruction transmitted by the prescription instruction data transmission unit is in stock, the delivery assistance unit 47 replaces the number of the stocks in the inventory with the number obtained after subtracting the number of the delivered contact lenses from the number of the stocks, and thereafter executes a delivery procedure to deliver a predetermined number of stocks of the contact lens to the affiliated facility associated with the affiliated facility terminal 35 requested from the prescription requesting unit 40.

It is to be noted that if the user ID code that meets the prerequisites and the data of the contact lens prescribed for the user last time are transmitted from the medical interview unit 50, the delivery assistance unit 47 executes a delivery procedure to deliver a contact lens corresponding to the data of the contact lens to the user.

The use fee settlement unit 48 includes a CPU. The use fee settlement unit 48 executes a settlement procedure for a use fee for the apparatus for optometric self-examination 32. The use fee settlement unit 48 executes a collection procedure from the user in regard to a use fee of an amount of money corresponding to the contents of the service provided from the apparatus for optometric self-examination 32 used by the user.

The affiliated facility terminal 35 includes a communication unit 49. The communication unit 49 includes a prescription instruction data reception unit for receiving the prescription instruction data transmitted by the prescription instruction data transmission unit from the management server 34.

Figure 7:
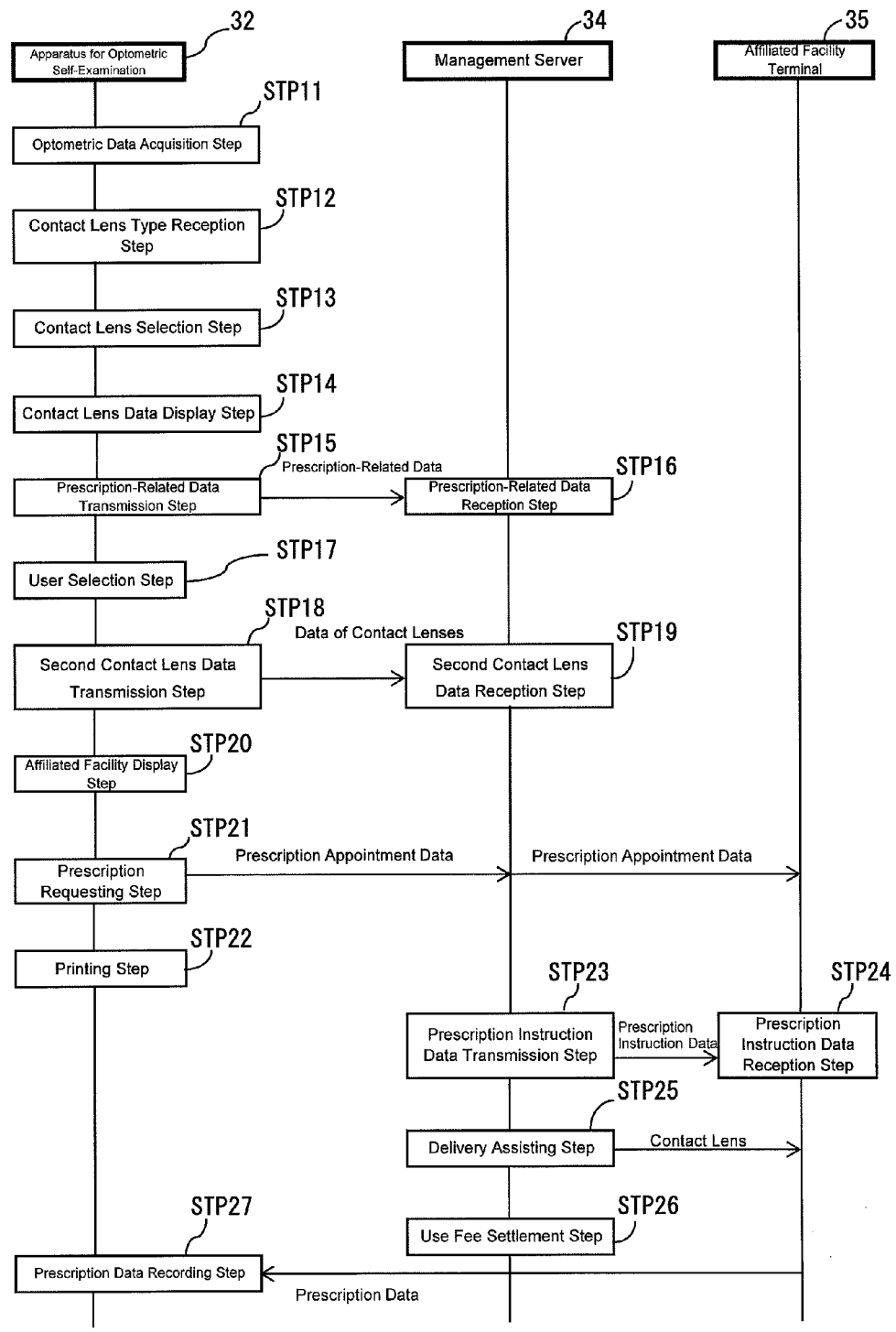
FIG. 7 is a sequence diagram illustrating an operational procedure of the contact lens selection system shown in FIG. 5.

Next, referring to FIG. 7, an operational procedure of the contact lens selection system 31 will be explained.

An optometric data acquisition step (STP 11) is a step of determining at least a part of a shape of a cornea of a user in response to an operation by the user and acquiring optometric data, based on the shape of the cornea. STP 11 is executed by the optometric data acquisition unit 2. STP 11 is executed according to a procedure similar to a procedure in STP 1.

A contact lens type reception step (STP 12) is a step of receiving an input of contact lens type data desired by the user. STP 12 is executed by the contact lens type reception unit 16. In STP 12, the contact lens type reception unit 16 receives, via the touchscreen 103, the user's demand in regard to a contact lens type including the type of general contact lenses for vision correction such as a hard type and a soft type; application mode such as daily wear, extended-wear and occasional use; service life such as disposable, planned replacement and long-term use; as well as intended usages such as bifocal and for keratoconus and for fashion. The contact lens type reception unit 16 may receive the user's demand by displaying various contact lens types on the touchscreen 103 and allowing the user to select a contact lens type therefrom, or may receive the user's demand by receiving a direct input from the user via the touchscreen 103.

A contact lens selection step (STP 13) is a step of selecting one or a plurality of contact lenses that match the contact lens type received in STP 12 and suited for the user. In STP 13, a contact lens is selected after a correction is made based on the data recorded by the prescription data recording unit 42. STP 13 is executed by the contact lens selection unit 39. Specifically, the contact lens selection unit 39 first extracts the maximum value and the minimum value among the curvature data at a plurality of points on the surface of the cornea of the user acquired in STP 11 and calculates an average value from the maximum value and the minimum value. The contact lens selection unit 39 selects (primarily selects) a base curve of a contact lens suitable for the user by multiplying the average value of the maximum value and the minimum value among the curvature data by the empirical parameter of a plurality of contact lenses recorded in the database 43. It is to be noted that the contact lens selection unit 39 may select a base curve after making a correction based on a value (correction value) obtained by subtracting the minimum value from the maximum value among the curvature data at the plurality of points acquired as the optometric data. Such a method of selection of a base curve is exemplified by a method including: calculating an average value from the maximum value and the minimum value among the curvature data at the plurality of points on the surface of the cornea of the user; multiplying the average value by the empirical parameter defined with respect to each contact lens; and thereafter adding the correction value.

Moreover, the contact lens selection unit 39 determines a dioptric power of the contact lenses such as a spherical dioptric power and an astigmatic dioptric power based on the eye refractive index data acquired by the optometric data acquisition unit 2. In the determination, the contact lens selection unit 39 may calculate spatial data of a space formed between the surface of the cornea of the user and the back face of the contact lens from the curvature data at a plurality of points on the surface of the cornea of the user and as the shape data of contact lenses 8 the data of a base curve of contact lenses recorded in the database 43, and then acquire the spatial data as data of a lacrimal fluid layer formed between the surface of the cornea of the user and the back face of the contact lens to determine the dioptric power of the contact lenses in light of the shape of the lacrimal fluid layer. Such a method for determining a dioptric power of the contact lenses is exemplified by a method including: assuming that an air layer, a contact lens layer, a lacrimal fluid layer and the cornea respectively constitute a lens group; simulating a total aberration in use of the contact lens; and determining a spherical dioptric power and an astigmatic dioptric power of a contact lens suitable for the user based on a result of such a simulation.

Furthermore, the contact lens selection unit 39 may calculate a refraction value in a state of the contact lens being applied to the eye by the user (over-refraction value) based on the optometric data, the spatial data and the shape data of the contact lens selected. In addition, the contact lens selection unit 39 may simulate visual performances in use of the contact lens based on the over-refraction value.

Moreover, contact lens selection unit 39 determines a diameter of the contact lens based on the data of the transverse corneal diameter of the user acquired by the optometric data acquisition unit 2. For example, in the case of hard contact lenses, the contact lens selection unit 39 defines as the diameter of the contact lens a value obtained by subtracting about 1.5 to 2.5 mm from the value of the data of the transverse corneal diameter acquired by the optometric data acquisition unit 2.

It is to be noted that the database 43 may store, as the shape data of contact lenses 8, a shape of a bevel of a plurality of contact lenses, and the contact lens selection unit 39 may select a contact lens in light of the shape of the bevel.

Next, in STP 13, an average of errors between values of the base curve of the primarily selected contact lenses and values of the base curve of the contact lenses actually and finally decided to be prescribed in the affiliated facility is calculated based on the prescription data 45, which is an accumulation of results of prescriptions executed in the past. Such an average of the errors can be determined by calculating an average of errors 45a recorded in prescription data 45. The contact lens selection unit 39 corrects a value of the base curve of the primarily selected contact lenses by such an average value of the errors, and selects (finally selects) a base curve of a final contact lens suited for the user. It is to be noted that such a correction may be made to the dioptric power, the diameter and the like of the contact lens in addition to the base curve of the contact lens.

Subsequently, the contact lens selection unit 39 selects, from among the contact lenses that match the contact lens type data received in STP 12, one or a plurality of contact lenses suited for a shape of the contact lens finally selected as a contact lens that matches the user, with reference to the shape data of contact lenses 8 and the contact lens type data 19.

A contact lens data display step (STP 14) is a step of displaying the data of the contact lenses selected in STP 13. STP 14 is executed by the contact lens data display unit 3. STP 14 is executed according to a procedure similar to a procedure in STP 3.

A prescription-related data transmission step (STP 15) is a step of transmitting via a network the optometric data acquired in STP 11 and the data of the contact lenses selected in STP 13 as the prescription-related data in relationship to the user identification data 20. STP 15 is executed by the communication unit 36. In STP 15, the communication unit 36 transmits the optometric data acquired in STP 11 and the data of the contact lenses selected in STP 13 to the management server 34 in relationship to the user identification data 20 of the user recorded in the database 43.

A prescription-related data reception step (STP 16) is a step of receiving the prescription-related data transmitted in STP 15. STP 16 is executed by the communication unit 46.

A user selection step (STP 17) is a step of allowing the user to select any contact lens from among a plurality of contact lenses displayed in STP 14. STP 17 is executed by the user selection unit 5. STP 17 is executed according to a procedure similar to a procedure in STP 4. STP 17 does not necessarily have to be executed after STP 16, as long as STP 17 is executed concomitantly with or after STP 14.

A second contact lens data transmission step (STP 18) is a step of transmitting the data of the contact lenses selected in STP 17 to the management server 34 in relationship to the user identification data 20 of the user stored in the database 43. STP 18 is executed by the communication unit 36. STP 18 may be executed concomitantly with STP 15. If STP 18 is executed concomitantly with STP 15, the communication unit 36 transmits the optometric data acquired in STP 11 and the data of the contact lenses selected in STP 13 as well as the data of the contact lenses selected in STP 17 to the management server 34 in relationship to the user identification data 20.

A second contact lens data reception step (STP 19) is a step of receiving the data of the contact lenses and user identification data transmitted in STP 18. STP 19 is executed by the communication unit 46.

An affiliated facility display step (STP 20) is a step of displaying the data of the affiliated facilities associated with the affiliated facility terminal 35. STP 20 is executed by the affiliated facility display unit 38. When an instruction to display affiliated facilities capable of prescribing a contact lens is conveyed from the user to the affiliated facility display unit 38 through touching of the touchscreen 103, the affiliated facility display unit 38 displays data of the affiliated facilities associated with the affiliated facility terminal 35 on the touchscreen 103 based on the affiliated facility data 44 stored in the database 43. Such data of the affiliated facilities are exemplified by an affiliated facility name, an address, contact information, an eye care practitioner who belongs to the affiliated facility, a fee structure including a charge of a contact lens, and the like. It is to be noted that the touchscreen 103 may be configured to display affiliated facility names and the like in a list, or to display only affiliated facilities in a specific area or affiliated facilities that charge a certain level of prescription fee or less according to the user's instruction and the like, or alternatively to display affiliated facilities near the installation site of the apparatus for optometric self-examination 32 intensively.

A prescription requesting step (STP 21) is a step of allowing the user to select any affiliated facility from the affiliated facilities displayed in STP 20, and requesting for a prescription with the affiliated facility in response to an operation by the user. STP 21 is executed by the prescription requesting unit 40. The prescription requesting unit 40 first displays the data of a plurality of affiliated facilities capable of prescribing a contact lens in STP 20. When the prescription requesting unit 40 receives from the user via the touchscreen 103 an input to the effect that the user has selected a certain affiliated facility, the prescription requesting unit 40 displays prescription available dates of the affiliated facility on the touchscreen 103. The prescription requesting unit 40 receives the date selected by the user, as the date appointed for prescription for the user, from among the prescription available dates displayed on the touchscreen 103. The date selected in STP 21 is communicated to at least the management server 34 and the affiliated facility terminal 35 requested for prescription, or uploaded such that the date can be freely viewed from the management server 34 and the affiliated facility terminal 35 requested for prescription.

A printing step (STP 22) is a step of printing the optometric data acquired in STP 11 and the data of the contact lenses selected in STP 13. STP 22 is executed by the printing unit 41. STP 22 is executed according to a procedure similar to a procedure in STP 5. Moreover, in STP 22, the date appointed for prescription in STP 21 may be printed.

A prescription instruction data transmission step (STP 23) is a step of transmitting prescription instruction data produced based on the prescription-related data received in STP 16 to an affiliated facility terminal 35 in an affiliated facility in which a prescription is executed. STP 23 is executed by the communication unit 46. When the communication unit 46 receives the prescription-related data from the apparatus for optometric self-examination 32, the communication unit 46 transmits a prescription instruction produced by an eye care practitioner and the like based on the prescription-related data to the affiliated facility terminal 35 in the affiliated facility that received the request for prescription in STP 21. It is to be noted that in STP 23, the prescription instruction is preferably produced with reference to the data of the contact lenses selected in STP 17 based on the user's preference and received in STP 19.

A prescription instruction data reception step (STP 24) is a step of receiving the prescription instruction data transmitted in STP 23. STP 24 is executed by the communication unit 49.

A delivery assisting step (STP 25) is a step of executing a delivery procedure to deliver a contact lens corresponding to the data of the contact lenses transmitted in STP 23 to the affiliated facility that received the request in STP 21. STP 25 is executed by the delivery assistance unit 47. In STP 25, the delivery assistance unit 47 first checks an inventory of the contact lenses managed by the management server 34 and hence stocks of the contact lenses recommended in the prescription instruction transmitted in STP 23. Thereafter, if the contact lens recommended in the prescription instruction transmitted in STP 23 is in stock, the delivery assistance unit 47 replaces the number of the stocks in the inventory with the number obtained after subtracting the number of the delivered contact lenses from the number of the stocks, and thereafter executes a delivery procedure to deliver a predetermined number of stocks of the contact lens to the affiliated facility associated with the affiliated facility terminal 35 requested in STP 21.

A use fee settlement step (STP 26) is a step of executing a settlement procedure for a use fee for the apparatus for optometric self-examination 32. STP 26 is executed by the use fee settlement unit 48. The use fee settlement unit 48 executes a collection procedure from the user in regard to a use fee of an amount of money corresponding to the contents of the service provided from the apparatus for optometric self-examination 32 used by the user.

A prescription data recording step (STP 27) is a step of recording a correlation between the data of the contact lenses selected in STP 13 and the data of the prescription executed by the affiliated facility that received the request in STP 21. STP 27 is executed by the prescription data recording unit 42. STP 27 is executed in that the prescription data recording unit 42 stores in the database 43 as the prescription data 45: a user ID code; an optometry apparatus ID code of the apparatus for optometric self-examination 32 used by the user; an affiliated facility ID code of the affiliated facility that has performed the prescription for the user; a value of the base curve of the contact lenses primarily selected by the apparatus for optometric self-examination 32 (primary selection value); and a value of a base curve of the contact lens decided to be prescribed in the affiliated facility (prescription decision value) in relationship to each other. Moreover, in STP 27, the prescription data recording unit 42 calculates an error between the primary selection value and the prescription decision value and records the error as an error 45*a*. It is to be noted that in STP 27, the respective data stored as the prescription data 45 do not need to be stored at the same time, and it is possible, for example, that the user ID code, the optometry apparatus ID code and the primary selection value are recorded after STP 13 and the prescription decision value decided to be prescribed in the affiliated facility that received the request for prescription in STP 21 and the affiliated facility ID code of the affiliated facility are recorded after STP 26.

It is to be noted that the contact lens selection system 31 may be constructed to receive from the user a reply to the medical interview data displayed by the medical interview unit 50 (medical interview step) instead of executing each step described above or according to the user's choice, as long as the user has utilized the contact lens selection system 31 within a predetermined period of time and has purchased or been prescribed with a contact lens. In this case, if the user's reply to the medical interview data meets prerequisites, the medical interview unit 50 transmits the user ID code of the user and the data of the contact lens prescribed for the user last time to the delivery assistance unit 47 in relationship to each other. Further, if the user ID code and the data of the contact lens prescribed for the user last time are transmitted, the delivery assistance unit 47 executes a delivery procedure to deliver a contact lens corresponding to the data of the contact lens to the user.

In regard to a user who has utilized the contact lens selection system 31 within a predetermined period of time and has purchased or been prescribed with a contact lens, the contact lens selection system 31 may provide a contact lens based on only a reply to a predetermined medical interview. As a result, the contact lens selection system can simplify the user's process of purchasing a contact lens. Moreover, the contact lens selection system can reduce a cost for optometry of the user and the like.

According to the apparatus for optometric self-examination 32, the user can obtain the optometric data acquired by the apparatus for optometric self-examination 32 and the data of the contact lens that matches the optometric data, and thereafter can request for a prescription with an affiliated facility along with an appointment of a desired date and time. Therefore, according to the apparatus for optometric self-examination 32, the user can visit the affiliated facility according to convenience to the user, a time period required for prescription in the affiliated facility can be shortened by utilizing the data obtained from the apparatus for optometric self-examination 32, and additionally a closer and more detailed prescription can be provided by the affiliated facility. Moreover, according to the apparatus for optometric self-examination 32, the affiliated facility can favorably compensate for lack of skill using the data obtained from the apparatus for optometric self-examination 32.

According to the apparatus for optometric self-examination 32, the prescription data recording unit 42 records the data of the contact lenses selected by the contact lens selection unit 39 and the data of the contact lens prescribed in the affiliated facility that received the request from the prescription requesting unit 40. Therefore, the apparatus for optometric self-examination 32 can determine an error bound for the contact lens selection unit 39 from a difference between the data of the contact lenses selected by the contact lens selection unit 39 and the data of the contact lens prescribed in the affiliated facility that received the request from the prescription requesting unit 40. Accordingly, according to the apparatus for optometric self-examination 32, due to the contact lens selection unit 39 making a correction based on such an error, fitting properties of the selected contact lens can be improved.

According to the management server 34, the prescription instruction data transmission unit can transmit via a network prescription instruction data produced based on the prescription-related data received by the prescription-related data reception unit. Therefore, according to the management server 34, due to an eye care practitioner who makes a prescription, and the like utilizing the prescription instruction data transmitted by the prescription instruction data transmission unit, a time period required for prescription for the user can be shortened, and additionally a closer and more detailed prescription can be provided for the user. Moreover, according to the management server 34, by transmitting the prescription instruction data to a predetermined contact lens store and the like via the prescription instruction data transmission unit, a contact lens suitable for the user can be selected or obtained without a need of prescription by an eye care practitioner.

The contact lens selection system 31 is readily available to even a new user through the user's own operation, and the user can find a contact lens suitable for the user. According to the contact lens selection system 31, since the contact lens selection unit 39 selects one or a plurality of contact lenses suited for the user based on the shape data 8 of a plurality of contact lenses stored in the database 43, lack of an eye care practitioner's skill can be favorably compensated for by storing in the database shape data of various contact lenses such as soft contact lenses and hard contact lenses, and a contact lens suitable for the user can be provided. According to the contact lens selection system 31, if an affiliated facility in which a prescription is executed utilizes the prescription instruction data transmitted by the prescription instruction data transmission unit, a reduction of a time period required for the prescription for the user and sophistication of the prescription for the user can be achieved, and additionally a process of purchase of a contact lens by the user can proceed smoothly.

The contact lens selection system 31 can produce prescription instruction data in light of the user's preference and thereafter transmit it to an affiliated facility. Therefore, according to the contact lens selection system 31, the affiliated facility can easily select a contact lens in light of the user's preference.

According to the contact lens selection system 31, the user can request for a prescription with an affiliated facility along with an appointment of a desired date and time. According to the contact lens selection system 31, in a case where the affiliated facility that received the request from the prescription requesting unit 40 utilizes the prescription instruction data received by the prescription instruction data reception unit, a prescription waiting time of the user and a time period required for prescription for the user can be shortened, and additionally a closer and more detailed prescription can be provided by the affiliated facility.

According to the contact lens selection system 31, the prescription data recording unit 42 records the data of the contact lenses selected by the contact lens selection unit 39 and the data of the contact lens prescribed in the affiliated facility that received the request from the prescription requesting unit 40. Therefore, the contact lens selection system 31 can determine an error bound for the contact lens selection unit 39 from difference between the data of the contact lenses selected by the contact lens selection unit 39 and the data of the contact lens prescribed in the affiliated facility that received the request from the prescription requesting unit 40. Accordingly, according to the contact lens selection system 31, due to the contact lens selection unit 39 making a correction based on such an error, fitting properties of the selected contact lens can be improved.

The contact lens selection system 31 can deliver a contact lens being likely to be purchased by the user to an affiliated facility in advance via the delivery assistance unit 47, and consequently a process of purchase of a contact lens by the user can proceed more smoothly. Moreover, according to the contact lens selection system 31, affiliated facility side does not need to order a necessary contact lens, and therefore an inventory control of contact lenses in the affiliated facility can be facilitated.

According to the contact lens selection system 31, the user can smoothly proceed with a payment procedure using the use fee settlement unit 48.

Figure 8:
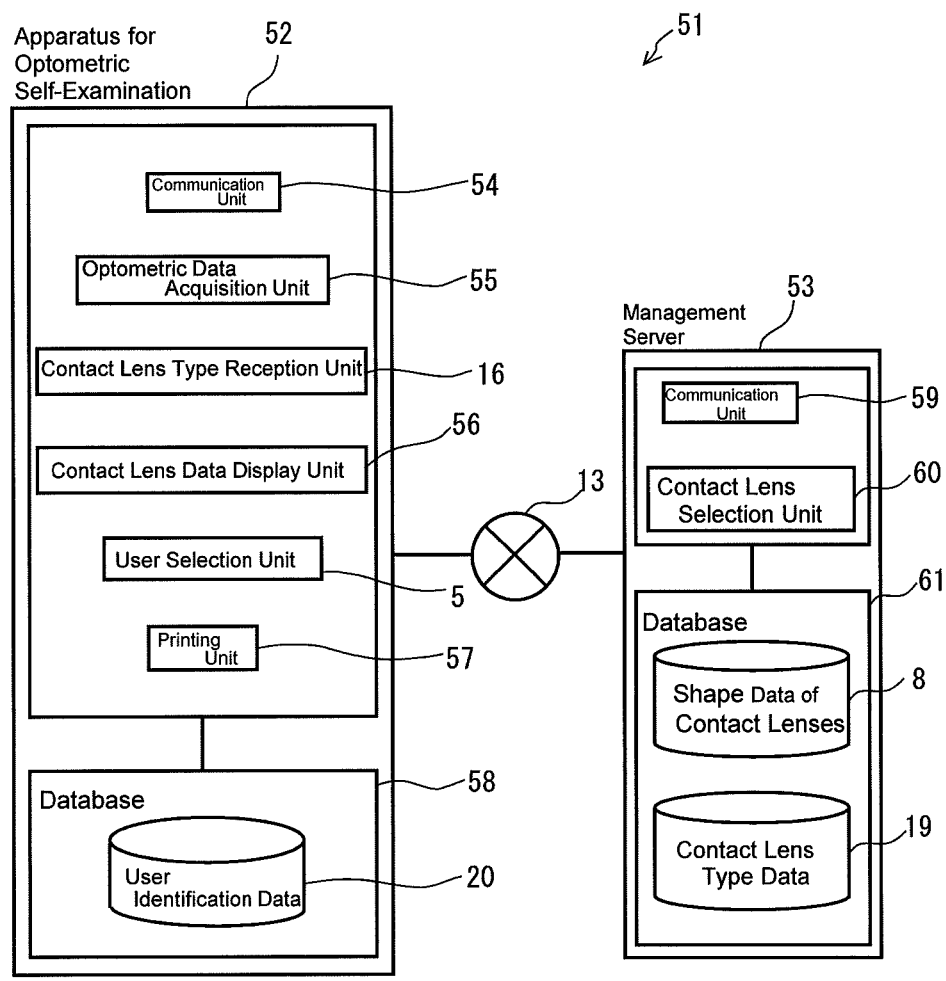
FIG. 8 is a schematic block diagram illustrating a contact lens selection system according to an embodiment different from the contact lens selection system shown in FIG. 4 or 5.

The contact lens selection system 51 shown in FIG. 8 includes an apparatus for optometric self-examination 52, a network 13, and a management server 53. The contact lens selection system 51 practically includes the apparatus for optometric self-examination 52 in a plurality of number. However, in FIG. 8, only one apparatus for optometric self-examination 52 is shown in order to avoid complication. Moreover, in the following description, the components identical to those of the apparatus for optometric self-examination 1 shown in FIG. 1, the contact lens selection system 11 shown in FIG. 4 and the contact lens selection system 31 shown in FIG. 5 are designated using the same number as in the Figures and explanation thereof will be omitted accordingly.

The apparatus for optometric self-examination 52 includes a communication unit 54, an optometric data acquisition unit 55, a contact lens type reception unit 16, a contact lens data display unit 56, a user selection unit 5, a printing unit 57, and a database 58. The apparatus for optometric self-examination 52 includes a basic data measurement terminal 101 and a user operation terminal 102, similarly to the apparatus for optometric self-examination 1 shown in FIG. 1.

The communication unit 54 controls network-communication between the apparatus for optometric self-examination 52 and an external apparatus such as the management server 53. The communication unit 54 transmits via a network the optometric data acquired by the optometric data acquisition unit 55 in relationship to the user identification data 20 of the user (optometric data transmission unit). The communication unit 54 transmits the contact lens type data received by the contact lens type reception unit 16 to the management server 53 in relationship to the user identification data 20 of the user (contact lens type data transmission unit). The communication unit 54 receives the data of the contact lenses that match the contact lens type data transmitted by the contact lens type data transmission unit and hence the one or a plurality of contact lenses selected based on the optometric data and the shape data of contact lenses 8 from the management server 53 (first contact lens data reception unit). The communication unit 54 transmits the data of the contact lenses selected by the user selection unit 5 to the management server 53 (second contact lens data transmission unit).

The optometric data acquisition unit 55 includes a corneal shape determination unit, a refractive index measurement unit, an analysis unit, and a CPU. The optometric data acquisition unit 55 determines a shape of a cornea of the user in response to an operation by the user, and acquires corneal shape data of the user as the optometric data. Specifically, when an instruction to acquire the optometric data is conveyed from the user through touching of the touchscreen 103, the optometric data acquisition unit 55 determines a shape of a cornea of the user via the corneal shape determination unit. Such a corneal shape is acquired by, for example, measuring curvature data at 1000 or more points on the surface of the cornea and performing an arithmetic processing. Moreover, the optometric data acquisition unit 55 measures a transverse corneal diameter of the user via the corneal shape determination unit and acquires data of the transverse corneal diameter. Furthermore, the optometric data acquisition unit 55 subjectively or objectively measures a refractive index of the eye of the user in response to an operation by the user via the refractive index measurement unit and acquires eye refractive index data.

The contact lens data display unit 56 includes a touchscreen 103 and a CPU. The contact lens data display unit 56 displays the data of one or a plurality of contact lenses received by the first contact lens data reception unit. Specifically, the contact lens data display unit 56 displays on the touchscreen 103 shape data 8 of one or a plurality of contact lenses selected by the contact lens selection unit 60 and received by the first contact lens data reception unit, as well as product data of the contact lenses such as a trade name, an item stock number and a price. Moreover, if the contact lens selection unit 60 has acquired data of the lacrimal fluid layer formed between the surface of the cornea of the user and the back face of the contact lens, the contact lens data display unit 56 displays on the touchscreen 103 a fluorescein pattern representing the shape of the lacrimal fluid layer. Furthermore, if the contact lens selection unit 60 has calculated a refraction value in a state of the contact lens being applied to the eye (over-refraction value), as described later, the contact lens data display unit 56 displays the over-refraction value on the touchscreen 103. In addition, if the contact lens selection unit 60 has simulated visual performances in use of the contact lens, the contact lens data display unit 56 displays a result of the simulation of the visual performances on the touchscreen 103.

The printing unit 57 includes a printer and a CPU. The printing unit 57 prints the optometric data acquired by the optometric data acquisition unit 55 and the data of one or a plurality of contact lenses received by the first contact lens data reception unit. When the printing unit 57 receives from the user via the touchscreen 103 an instruction to print the optometric data acquired by the optometric data acquisition unit 55 and the data of the contact lenses selected by the contact lens selection unit 60 and received by the first contact lens data reception unit, the printing unit 57 prints these data on a predetermined form. The data of the contact lenses printed by the printing unit 57 are ejected from the paper ejection unit 104. The data of the contact lenses printed by the printing unit 57 may have been received in advance by the first contact lens data reception unit, or alternatively may be received by the contact lens data reception unit after the printing unit 57 receives an instruction of printing from the user. Moreover, the printing unit 57 does not necessarily print both the optometric data and the data of the contact lenses, and may print only the optometric data or only the data of the contact lenses according to the user's choice, the content of the service or the like. Furthermore, the printing unit 57 may be configured to print the data of the contact lenses selected by the user selection unit 5. The printing unit 57 may include a photographic printing unit.

The database 58 contains user identification data 20.

The management server 53 includes a communication unit 59, a contact lens selection unit 60, and a database 61. The management server 53 may be constituted of one or a plurality of computers. Moreover, the management server 53 may include a certain input apparatus, and the like.

The communication unit 59 controls network-communication between the management server 53 and an external apparatus such as the apparatus for optometric self-examination 52. The communication unit 59 receives the optometric data and the user identification data transmitted from the apparatus for optometric self-examination 52 (optometric data reception unit). The communication unit 59 receives the contact lens type data and the user identification data 20 transmitted by the contact lens type data transmission unit (contact lens type data reception unit). The communication unit 59 transmits data of the contact lenses selected by the contact lens selection unit 60 to the apparatus for optometric self-examination 52 (first contact lens data transmission unit). The communication unit 59 transmits via a network prescription instruction data produced based on the optometric data received by the optometric data reception unit and the data of the contact lenses selected by the contact lens selection unit 60 (prescription instruction data transmission unit). The communication unit 59 receives the data of the contact lenses transmitted by the second contact lens data transmission unit (second contact lens data reception unit).

The contact lens selection unit 60 includes a CPU. The contact lens selection unit 60 selects one or a plurality of contact lenses suited for the optometric data, based on the optometric data and the shape data 8 of contact lenses stored in the database 61. Moreover, the contact lens selection unit 60 selects contact lenses that match the contact lens type data received by the contact lens type data reception unit. Specifically, the contact lens selection unit 60 first acquires the optometric data of the user transmitted from the apparatus for optometric self-examination 52 by the optometric data transmission unit and received by the management server 53 via the optometric data reception unit. Next, the contact lens selection unit 60 acquires data of a base curve of a plurality of contact lenses stored in the database 58. The contact lens selection unit 60 calculates, from the corneal shape data of the user and the data of the base curve of the plurality of contact lenses acquired, a plurality of distances along normal lines to the back face of the contact lens respectively drawn from a plurality of points on the surface of the cornea of the user. The contact lens selection unit 60 selects, as the base curve of a contact lens suited for the user, a base curve that gives a small difference between these distances along the normal directions. According to the management server 53, the contact lens selection unit 60 selects a base curve of a contact lens based on the distance from cornea surface of the user to the back face of the contact lens along a normal direction, and therefore fitting properties of the selected contact lens to the user can be further improved.

Moreover, the contact lens selection unit 60 determines a dioptric power of the contact lenses such as a spherical dioptric power and an astigmatic dioptric power based on the eye refractive index data acquired by the optometric data acquisition unit 55. According to the management server 53, due to the contact lens selection unit 60 determining the dioptric power of the contact lenses based on the eye refractive index data, a dioptric power of a contact lens suitable for the user can be easily and rapidly determined. Moreover, the contact lens selection unit 60 may calculate spatial data of a space formed between the surface of the cornea of the user and the back face of the contact lens from the plurality of distances along normal lines to the back face of the contact lens respectively drawn from a plurality of points on the surface of the cornea of the user, acquire the spatial data as data of a lacrimal fluid layer formed between the surface of the cornea of the user and the back face of the contact lens, and determine the dioptric power of the contact lenses in light of the shape of the lacrimal fluid layer. Such a method for determining a dioptric power of the contact lenses is exemplified by a method including assuming that an air layer, a contact lens layer, a lacrimal fluid layer and the cornea respectively constitute a lens group, simulating a total aberration in use of the contact lens aberration and determining a spherical dioptric power and an astigmatic dioptric power of a contact lens suitable for the user based on a result of such a simulation. According to the management server 53, accuracy of the dioptric power of the contact lenses selected by the contact lens selection unit 60 can be further improved by determining the dioptric power of the contact lenses in light of the shape of the lacrimal fluid layer as described above.

Furthermore, the contact lens selection unit 60 may calculate a refraction value in a state of the contact lens being applied to the eye by the user (over-refraction value) based on the optometric data, the spatial data and the shape data of the contact lens selected. In addition, the contact lens selection unit 60 may simulate visual performances in use of the contact lens based on the over-refraction value.

Moreover, the contact lens selection unit 60 determines a diameter of the contact lens based on the data of the transverse corneal diameter of the user acquired by the optometric data acquisition unit 55. For example, in the case of hard contact lenses, the contact lens selection unit 60 defines as the diameter of the contact lens a value obtained by subtracting about 1.5 to 2.5 mm from the value of the data of the transverse corneal diameter acquired by the optometric data acquisition unit 55. The management server 53 thus determines the diameter of the contact lens based on the data of the transverse corneal diameter acquired by the optometric data acquisition unit 55, whereby the diameter of a contact lens suitable for the user can be easily and rapidly selected.

It is to be noted that the database 61 may store, as the shape data of contact lenses 8, a shape of a bevel of a plurality of contact lenses, and the contact lens selection unit 60 may select a contact lens in light of the shape of the bevel.

The contact lens selection unit 60 selects, from among the contact lenses that match the contact lens type data received by the contact lens type data reception unit, one or a plurality of contact lenses suited for the base curve, the dioptric power, the diameter and the like of the contact lenses selected as described above as a contact lens that matches the user, with reference to the shape data of contact lenses 8 and the contact lens type data 19.

The database 61 contains shape data of contact lenses 8 and contact lens type data 19.

Figure 9:
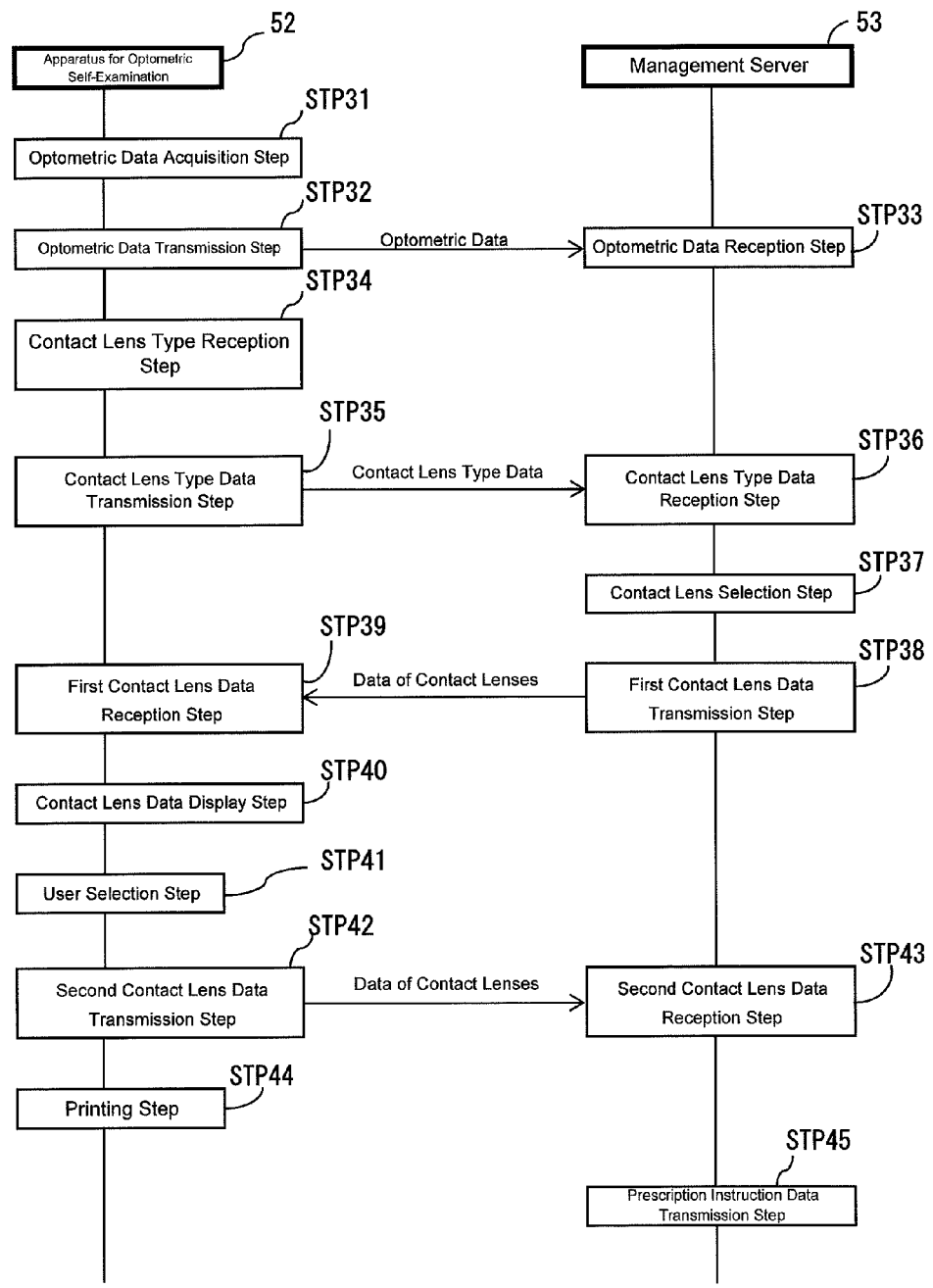
FIG. 9 is a sequence diagram illustrating an operational procedure of the contact lens selection system shown in FIG. 8.

Subsequently, referring to FIG. 9, an operational procedure of the contact lens selection system 51 will be explained.

An optometric data acquisition step (STP 31) is a step of determining a shape of a cornea of a user in response to an operation by the user and acquiring corneal shape data of the user as optometric data. STP 31 is executed by the optometric data acquisition unit 55. In STP 31, when an instruction to acquire the optometric data is conveyed from the user through touching of the touchscreen 103, the optometric data acquisition unit 55 determines a shape of a cornea of the user via the corneal shape determination unit. Such a corneal shape is acquired by, for example, measuring curvature data at 1000 or more points on the surface of the cornea and performing an arithmetic processing. Moreover, the optometric data acquisition unit 55 measures a transverse corneal diameter of the user via the corneal shape determination unit and acquires data of the transverse corneal diameter. Furthermore, the optometric data acquisition unit 55 subjectively or objectively measures a refractive index of the eye of the user in response to an operation by the user via the refractive index measurement unit and acquires eye refractive index data.

An optometric data transmission step (STP 32) is a step of transmitting the optometric data acquired in STP 31 to the management server 53 in relationship to user identification data 20 of the user stored in the database 58. STP 32 is executed by the communication unit 54. It is to be noted that in STP 32, the optometric data acquired in STP 31 and the user identification data 20 of the user stored in the database 58 may be transmitted via a network to an external apparatus other than the server 43 such as a personal computer of the user.

An optometric data reception step (STP 33) is a step of receiving the optometric data and the user identification data 20 transmitted in STP 32. STP 33 is executed by the communication unit 59.

A contact lens type reception step (STP 34) is a step of receiving a contact lens type desired by the user. STP 34 is executed by the contact lens type reception unit 16. STP 34 is executed according to a procedure similar to a procedure in STP 12.

A contact lens type data transmission step (STP 35) is a step of transmitting the contact lens type data received in STP 34 to the management server 53. STP 35 is executed by the communication unit 54.

A contact lens type data reception step (STP 36) is a step of receiving the contact lens type data transmitted in STP 35. STP 36 is executed by the communication unit 59.

A contact lens selection step (STP 37) is a step of selecting one or a plurality of contact lenses that match the contact lens type received in STP 36 and suited for the user. STP 37 is executed by the contact lens selection unit 60. In STP 37, the contact lens selection unit 60 first acquires the optometric data of the user received in STP 33. Next, the contact lens selection unit 60 acquires data of a base curve of a plurality of contact lenses stored in the database 58 as the shape data of contact lenses 8. The contact lens selection unit 60 calculates, from the corneal shape data of the user and the data of a base curve of the plurality of contact lenses acquired, a plurality of distances along normal lines to the back face of the contact lens respectively drawn from a plurality of points on the surface of the cornea of the user. The contact lens selection unit 60 selects, as the base curve of the contact lens suited for the user, a base curve that gives a small difference between these distances along the normal directions.

Moreover, the contact lens selection unit 60 determines a dioptric power of the contact lenses such as a spherical dioptric power and an astigmatic dioptric power based on the eye refractive index data acquired in STP 31. In the determination, the contact lens selection unit 60 may calculate spatial data of a space formed between the surface of the cornea of the user and the back face of the contact lens from a plurality of distances along normal lines to the back face of the contact lens respectively drawn from a plurality of points on the surface of the cornea of the user, acquire the spatial data as data of a lacrimal fluid layer formed between the surface of the cornea of the user and the back face of the contact lens, and determine the dioptric power of the contact lenses in light of the shape of the lacrimal fluid layer. Such a method for determining a dioptric power of the contact lenses is exemplified by a method including assuming that an air layer, a contact lens layer, a lacrimal fluid layer and the cornea respectively constitute a lens group, simulating a total aberration in use of the contact lens and determining a spherical dioptric power and an astigmatic dioptric power of a contact lens suitable for the user based on a result of such a simulation.

Furthermore, the contact lens selection unit 60 may calculate a refraction value in a state of the contact lens being applied to the eye by the user (over-refraction value) based on the optometric data, the spatial data and the shape data of the contact lens selected. In addition, the contact lens selection unit 60 may simulate visual performances in use of the contact lens based on the over-refraction value.

Moreover, the contact lens selection unit 60 determines a diameter of the contact lens based on the data of the transverse corneal diameter of the user acquired in STP 31. For example, in the case of hard contact lenses, the contact lens selection unit 60 defines as the diameter of the contact lens a value obtained by subtracting about 1.5 to 2.5 mm from the value of the data of the transverse corneal diameter acquired by the optometric data acquisition unit 55.

It is to be noted that the database 61 may store, as the shape data of contact lenses 8, a shape of a bevel of a plurality of contact lenses, and the contact lens selection unit 60 may select a contact lens in light of the shape of the bevel.

Subsequently, the contact lens selection unit 60 selects, from among the contact lenses that match the contact lens type data received in STP 36, one or a plurality of contact lenses suited for the base curve, the dioptric power, the diameter and the like of the contact lenses selected as described above as a contact lens that matches the user with reference to the shape data of contact lenses 8 and the contact lens type data 19.

A first contact lens data transmission step (STP 38) is a step of transmitting the data of the contact lenses selected in STP 37 to the apparatus for optometric self-examination 52. STP 38 is executed by the communication unit 59. It is to be noted that if the contact lens selection unit 60 has acquired data of the lacrimal fluid layer formed between the surface of the cornea of the user and the back face of the contact lens in STP 37, the communication unit 59 transmits data of the fluorescein pattern representing the shape of the lacrimal fluid layer to the apparatus for optometric self-examination 52 in STP 38. Moreover, if the contact lens selection unit 60 has calculated the over-refraction value in STP 37, the communication unit 59 transmits data of the over-refraction value to the apparatus for optometric self-examination 52 in STP 38. In addition, if the contact lens selection unit 60 has been simulated the visual performances in use of the contact lens based on the over-refraction value in STP 37, the communication unit 59 transmits data of a result of the simulation of the visual performances to the apparatus for optometric self-examination 52 in STP 38.

A first contact lens data reception step (STP 39) is a step of receiving the data of the contact lenses selected in STP 37 and transmitted in STP 38. STP 39 is executed by the communication unit 54. It is to be noted that if the data of the fluorescein pattern has been transmitted in STP 38, such data of the fluorescein pattern is also received in STP 39. Moreover, if the data of the over-refraction value has been transmitted in STP 38, such data of the over-refraction value is also received in STP 39. Furthermore, if the result of the simulation of the visual performances has been transmitted in STP 38, such data of the result of the simulation of the visual performances is also received in STP 39.

A contact lens data display step (STP 40) is a step of displaying the data of the contact lenses received in STP 39. STP 40 is executed by the contact lens data display unit 56. Specifically, the contact lens data display unit 56 displays on the touchscreen 103 the shape data 8 of the one or a plurality of contact lenses selected in STP 37 and received in STP 39 as well as product data of the contact lenses such as a trade name, an item stock number and a price. It is to be noted that if the contact lens data display unit 56 has received the data of the fluorescein pattern in STP 39, the contact lens data display unit 56 also displays such data on the touchscreen 103. Moreover, if the contact lens data display unit 56 has received the data of the over-refraction value in STP 39, the contact lens data display unit 56 also displays such data of the over-refraction value on the touchscreen 103. In addition, if the contact lens data display unit 56 has received the data of the result of the simulation of the visual performances in STP 39, the contact lens data display unit 56 displays the data of the result of the simulation of the visual performances on the touchscreen 103 as well.

A user selection step (STP 41) is a step of allowing the user to select any contact lens from among a plurality of contact lenses displayed in STP 40. STP 41 is executed by the user selection unit 5. STP 41 is executed according to a procedure similar to a procedure in STP 4.

A second contact lens data transmission step (STP 42) is a step of transmitting data of the contact lenses selected in STP 41 to the management server 53. STP 42 is executed by the communication unit 54.

A second contact lens data reception step (STP 43) is a step of receiving the data of the contact lens transmitted in STP 42. STP 43 is executed by the communication unit 59.

A printing step (STP 44) is a step of printing the optometric data acquired in STP 31 and the data of the contact lenses received in STP 39. STP 44 is executed by the printing unit 57. When the printing unit 57 receives from the user via the touchscreen 103 an instruction to print the optometric data acquired in STP 31 and the data of the contact lenses received in STP 39, the printing unit 57 prints these data on a predetermined form. The data of the contact lenses printed in STP 44 are ejected from the paper ejection unit 104. It is to be noted that the data of the contact lenses printed in STP 44 may have been received in advance by the first contact lens data reception unit, or alternatively may be received by the contact lens data reception unit after the printing unit 57 receives an instruction of printing from the user. Moreover, in STP 44, it is not necessary to print both the optometric data and the data of the contact lenses, and only the optometric data or only the data of the contact lenses may be printed according to the user's choice, the content of the service or the like. Furthermore, in STP 44, the data of the contact lenses selected by the user selection unit 5 may be printed.

A prescription instruction data transmission step (STP 45) is a step of transmitting via a network prescription instruction data produced based on the optometric data received in STP 33 and the data of the contact lenses selected in STP 37. STP 45 is executed by the communication unit 59. The communication unit 59 transmits via a network a prescription instruction produced by an eye care practitioner and the like based on the optometric data received in STP 33 and the data of the contact lenses selected in STP 37. It is to be noted that in STP 45, the prescription instruction is preferably produced with reference to the data of the contact lenses selected in STP 41 based on the user's preference and transmitted in STP 42.

The apparatus for optometric self-examination 52 can transmit the optometric data and the user identification data to an external apparatus capable of communicating via a network with the apparatus for optometric self-examination 52 via a network by means of the optometric data transmission unit. As a result, the apparatus for optometric self-examination 52 can select a contact lens suitable for the user using such an external apparatus.

The management server 53 can select one or a plurality of contact lenses suited for the user based on the shape data 8 of a plurality of contact lenses stored in the database 61. The management server 53 can favorably compensate for lack of an eye care practitioner's skill by storing the shape data 8 of various contact lenses such as soft contact lenses and hard contact lenses in the database 61, and a contact lens suitable for the user can be provided.

The management server 53 enables the user to visually recognize the fluorescein pattern transmitted by the first contact lens data transmission unit, by allowing the apparatus for optometric self-examination 52 that has received the fluorescein pattern to display the fluorescein pattern. As a result, according to the management server 53, the user can ascertain the fluorescein pattern without using a trial lens. Moreover, according to such a constitution, the user can visually ascertain fitting properties of the contact lens, and consequently a comfort level of the user can be enhanced.

The management server 53 can display the over-refraction value by means of the apparatus for optometric self-examination 52 that has received the over-refraction value transmitted by the first contact lens data transmission unit. As a result, the management server 53 can display validity of the contact lenses selected by the contact lens selection unit 60 to the user, and consequently a comfort level of the user can be enhanced.

The management server 53 can display the result of the simulation of the visual performances by means of the apparatus for optometric self-examination 52 that has received the data of the result of the simulation of the visual performances transmitted by the first contact lens data transmission unit. As a result, according to the management server 53, a comfort level of the user can be further enhanced.

According to the management server 53, it is possible to select a contact lens in accordance with preference of the user, since the contact lens selection unit 60 selects contact lenses that match the contact lens type data received by the contact lens type data reception unit.

Since the management server 53 includes the prescription instruction data transmission unit for transmitting via a network prescription instruction data produced based on the optometric data and the data of the contact lenses selected by the contact lens selection unit 60, easiness, preciseness and rapidity of the prescription of the contact lens can be improved.

The contact lens selection system 51 is readily available to even a new user through the user's own operation, and the user can find a contact lens suitable for the user. Moreover, according to the contact lens selection system 51, if an eye care practitioner uses the optometric data acquired by the optometric data acquisition unit 55 and the data of the contact lenses displayed by the contact lens data display unit 56, a time period required by the eye care practitioner for prescription can be shortened. According to the contact lens selection system 51, since the contact lens selection unit 60 selects one or a plurality of contact lenses suited for the user based on the shape data 8 of a plurality of contact lenses stored in the database 61, lack of an eye care practitioner's skill can be favorably compensated for by storing the shape data 8 on various contact lenses such as soft contact lenses and hard contact lenses in the database 61, and a contact lens suitable for the user can be provided.

According to the contact lens selection system 51, since the user can select any contact lens from among a plurality of contact lenses displayed by the contact lens data display unit 56, the user can easily select a contact lens suitable for the user and preferred by the user without visiting an eye care practitioner or the like.

The contact lens selection system 51 includes the printing unit 57. Therefore, according to the contact lens selection system 51, the user can ascertain the user's own optometric data and the data of a contact lens suitable for the user any time. Furthermore, according to the contact lens selection system 51, the user can visit a contact lens store and the like with these data held in the user's hand and purchase the desired contact lens, or alternatively can visit an eye care practitioner and the like with these data held in the user's hand and receive more detailed prescription.

Figure 10:
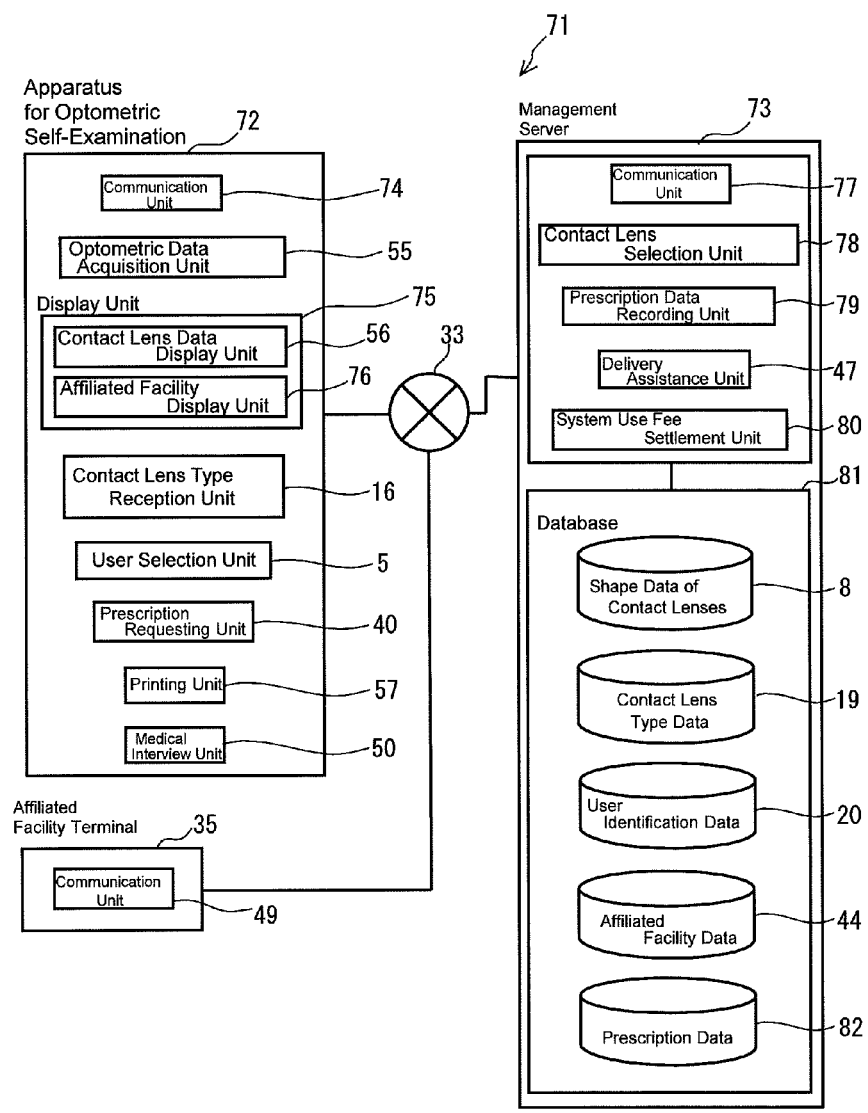
FIG. 10 is a schematic block diagram illustrating a contact lens selection system according to an embodiment different from the contact lens selection system shown in FIGS. 4, 5 and 8.

The contact lens selection system 71 shown in FIG. 10 includes an apparatus for optometric self-examination 72, a network 33, a management server 73 and an affiliated facility terminal 35. The contact lens selection system 71 practically includes the apparatus for optometric self-examination 72 and the affiliated facility terminal 35 in a plurality of number. However, in FIG. 10, only one apparatus for optometric self-examination 72 and only one affiliated facility terminal 35 are shown in order to avoid complication. Moreover, in the following description, the components identical to those of the aforementioned apparatus for optometric self-examination 1 and the contact lens selection systems 11, 31 and 51 are designated using the same number as in these apparatuses for optometric self-examination and the contact lens selection systems, and explanation thereof will be omitted accordingly.

The apparatus for optometric self-examination 72 includes a communication unit 74, an optometric data acquisition unit 55, a display unit 75, a contact lens type reception unit 16, a user selection unit 5, a prescription requesting unit 40, a printing unit 57, and a medical interview unit 50. The apparatus for optometric self-examination 72 includes a basic data measurement terminal 101 and a user operation terminal 102, similarly to the apparatus for optometric self-examination 1 shown in FIG. 1.

The communication unit 74 controls network-communication among the apparatus for optometric self-examination 72, the management server 73 and an external apparatus such as the affiliated facility terminal 35. The communication unit 74 transmits the optometric data acquired by the optometric data acquisition unit 55 to the management server 73 in relationship to the user identification data 20 of the user (optometric data transmission unit). The communication unit 74 transmits the contact lens type data received by the contact lens type reception unit 16 to the management server 73 in relationship to the user identification data 20 of the user (contact lens type data transmission unit). The communication unit 74 receives from the management server 73 the data of the contact lenses that match the contact lens type data transmitted by the contact lens type data transmission unit and hence the contact lenses selected by the contact lens selection unit 78 based on the optometric data and the shape data of contact lenses (first contact lens data reception unit). The communication unit 74 transmits the data of the contact lenses selected by the user selection unit 5 to the management server 73 in relationship to the user identification data 20 of the user stored in the database 81 (second contact lens data transmission unit).

The display unit 75 includes a contact lens data display unit 56 and an affiliated facility display unit 76. The display unit 75 includes a touchscreen 103 and a CPU. The affiliated facility display unit 76 displays data of the affiliated facilities associated with the affiliated facility terminal 35. Specifically, when an instruction to display affiliated facilities capable of prescribing a contact lens is conveyed from the user to the affiliated facility display unit 76 through touching of the touchscreen 103, the affiliated facility display unit 76 acquires affiliated facility data 44 stored in the database 81, and displays data of the affiliated facilities associated with the affiliated facility terminal 35 on the touchscreen 103.

The management server 73 includes a communication unit 77, a contact lens selection unit 78, a prescription data recording unit 79, a delivery assistance unit 47, a system use fee settlement unit 80, and a database 81.

The communication unit 77 controls network-communication among the management server 73, the apparatus for optometric self-examination 72 and an external apparatus such as the affiliated facility terminal 35. The communication unit 77 receives the optometric data and the user identification data 20 transmitted by the optometric data transmission unit from the apparatus for optometric self-examination 72 (optometric data reception unit). The communication unit 77 receives the contact lens type data and user identification data 20 transmitted by the contact lens type data transmission unit (contact lens type data reception unit). The communication unit 77 transmits data of the contact lenses selected by the contact lens selection unit 78 to the apparatus for optometric self-examination 72 (first contact lens data transmission unit). The communication unit 77 transmits prescription instruction data produced based on the optometric data received by the optometric data reception unit and the data of the contact lenses selected by the contact lens selection unit 78 to an affiliated facility terminal 35 in an affiliated facility in which a prescription is executed (prescription instruction data transmission unit). The communication unit 77 receives the data of the contact lens transmitted by the second contact lens data transmission unit and the user identification data 20 (second contact lens data reception unit).

The contact lens selection unit 78 includes a CPU. The contact lens selection unit 78 selects contact lenses that match the contact lens type data received by the contact lens type data reception unit. The process in which the contact lens selection unit 78 selects contact lenses that match the contact lens type data received by the contact lens type data reception unit is similar to that for the contact lens selection unit 17. Moreover, the contact lens selection unit 78 selects a contact lens after making a correction with respect to each user based on the data recorded by the prescription data recording unit 79. Specifically, the contact lens selection unit 78 first acquires the optometric data of the user transmitted from the apparatus for optometric self-examination 52 by the optometric data transmission unit and received by the management server 73 by the optometric data reception unit.

Next, the contact lens selection unit 78 acquires data of a base curve of a plurality of contact lenses stored in the database 81 as the shape data 8 of contact lenses. The contact lens selection unit 78 calculates, from the corneal shape data of the user and the data of a base curve of the plurality of contact lenses acquired, a plurality of distances along the normal lines to the back face of the contact lens respectively drawn from a plurality of points on the surface of the cornea of the user. The contact lens selection unit 78 selects (primarily selects), as the base curve of the contact lens suited for the user, a base curve that gives a small difference between these distances along the normal directions.

Next, the contact lens selection unit 78 determines a dioptric power of the contact lenses such as a spherical dioptric power and an astigmatic dioptric power based on the eye refractive index data received by the optometric data reception unit. Alternatively, the contact lens selection unit 78 may calculate spatial data of a space formed between the surface of the cornea of the user and the back face of the contact lens from a plurality of distances along normal lines to the back face of the contact lens respectively drawn from a plurality of points on the surface of the cornea of the user, acquire the spatial data as data of a lacrimal fluid layer formed between the surface of the cornea of the user and the back face of the contact lens, and determine the dioptric power of the contact lenses in light of the shape of the lacrimal fluid layer. Such a method for determining a dioptric power of the contact lenses is exemplified by a method including assuming that an air layer, a contact lens layer, a lacrimal fluid layer and the cornea respectively constitute a lens group, simulating a total aberration in use of the contact lens and determining a spherical dioptric power and an astigmatic dioptric power of a contact lens suitable for the user based on a result of such a simulation.

Furthermore, the contact lens selection unit 78 may calculate a refraction value in a state of the contact lens being applied to the eye by the user (over-refraction value) based on the optometric data, the spatial data and the shape data of the contact lens selected. In addition, the contact lens selection unit 78 may simulate visual performances in use of the contact lens based on the over-refraction value.

Moreover, the contact lens selection unit 78 determines a diameter of the contact lens based on the data of the transverse corneal diameter received by the optometric data reception unit. For example, in the case of hard contact lenses, the contact lens selection unit 78 defines as the diameter of the contact lens a value obtained by subtracting about 1.5 to 2.5 mm from the value of the data of the transverse corneal diameter received by the optometric data reception unit.

It is to be noted that the database 81 may store, as the shape data of contact lenses 8, a shape of a bevel of a plurality of contact lenses, and the contact lens selection unit 78 may select a contact lens in light of the shape of the bevel.

Subsequently, the contact lens selection unit 78 calculates, based on prescription data 82 that include accumulated results of prescriptions executed in the past with respect to the user, an average of errors between values of the base curve of the primarily selected contact lenses and values of the base curve of the contact lenses actually and finally decided to be prescribed in the affiliated facility. Such an average of the errors can be determined from an averaged error 82a of the prescription data 82. The contact lens selection unit 78 corrects the value of the base curve of the primarily selected contact lenses by such an average of the errors, and selects (finally selects) one or a plurality of final contact lenses suited for the user. It is to be noted that such a correction may be made to the dioptric power, the diameter and the like of the contact lens in addition to the base curve of the contact lens.

The prescription data recording unit 79 includes a CPU. The prescription data recording unit 79 records the data of the contact lenses selected by the contact lens selection unit 78 and the data of the prescription executed by the affiliated facility that received the request from the prescription requesting unit 40 in relationship to the user identification data. Specifically, the prescription data recording unit 79 first records the value of the base curve of the contact lenses primarily selected by the contact lens selection unit 78 (primary selection value) in the database 81 in relationship to the user ID code of the user. Next, the prescription data recording unit 79 receives from the affiliated facility terminal 35 a value of a base curve of the contact lens decided to be prescribed in the affiliated facility that received the request from the prescription requesting unit 40 (prescription decision value) and the affiliated facility ID code of the affiliated facility, and records them in the database 81 in relationship to the user ID code and the primary selection value recorded first. These data recorded by the prescription data recording unit 79 are organized with respect to each user ID code, and stored in the database 81 as the prescription data 82 of each user.

The system use fee settlement unit 80 includes a CPU. The system use fee settlement unit 80 executes a settlement procedure for a system use fee including a use fee for the apparatus for optometric self-examination 72 and a purchase price of a contact lens obtained via the contact lens selection system 71 under assumption of a lump sum payment thereof. Specifically, the system use fee settlement unit 80 displays on the touchscreen 103 a use fee for the apparatus for optometric self-examination 72 set in accordance with the content of the service and the like and a purchase cost of a contact lens in an affiliated facility set based on the prescription instruction data produced by the management server 73 and the like. If the system use fee settlement unit 80 receives approval of payment for the system use fee displayed on the touchscreen 103 from the user via the touchscreen 103, the system use fee settlement unit 80 executes a settlement procedure under assumption of the payment on the date scheduled for prescription by way of the prescription requesting unit 40. Such a system use fee including the use fee for the apparatus for optometric self-examination 72 and the purchase price of the contact lens obtained via the contact lens selection system 71 is collected in a lump sum by an administrator of the management server 73.

The database 81 contains shape data of contact lenses 8, contact lens type data 19, user identification data 20, affiliated facility data 44, and prescription data 82.

Figure 11:
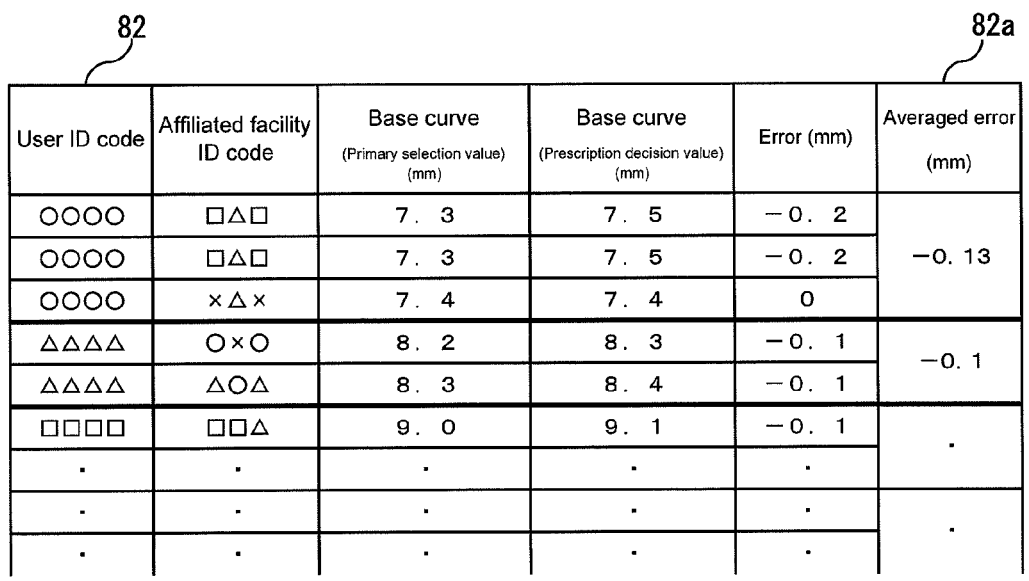
FIG. 11 is a diagram illustrating an example of prescription data in the contact lens selection system shown in FIG. 10.

As the prescription data 82, a value of the base curve of the contact lenses primarily selected by the contact lens selection unit 78; a value of a base curve of the contact lens decided to be prescribed in the affiliated facility that received the request from the prescription requesting unit 40; an affiliated facility ID code of an affiliated facility that has determined the prescription; and an error between the primary selection value and the prescription decision value, are recorded in relationship to the user ID code. Specifically, the following are stored line-by-line in the following order in the prescription data 82: a user ID code of a specific user; an affiliated facility ID code to identify the affiliated facility that received the request from the user via the prescription requesting unit 40; a value of the base curve of the contact lenses primarily selected by the contact lens selection unit 78 (primary selection value); a value of a base curve of the contact lens decided to be prescribed in the affiliated facility that received the request from the prescription requesting unit 40 (prescription decision value); and an error between the primary selection value and the prescription decision value, as shown in FIG. 11. Moreover, an averaged error 82a between the primary selection values calculated with respect to each user and the prescription decision values is recorded in the prescription data 82. The prescription data 82 is assembled with respect to each identical user ID code. It is to be noted that the dioptric power, the diameter and the like of the contact lens may be included in the prescription data 82 in addition to a base curve of a contact lens.

Figure 12:
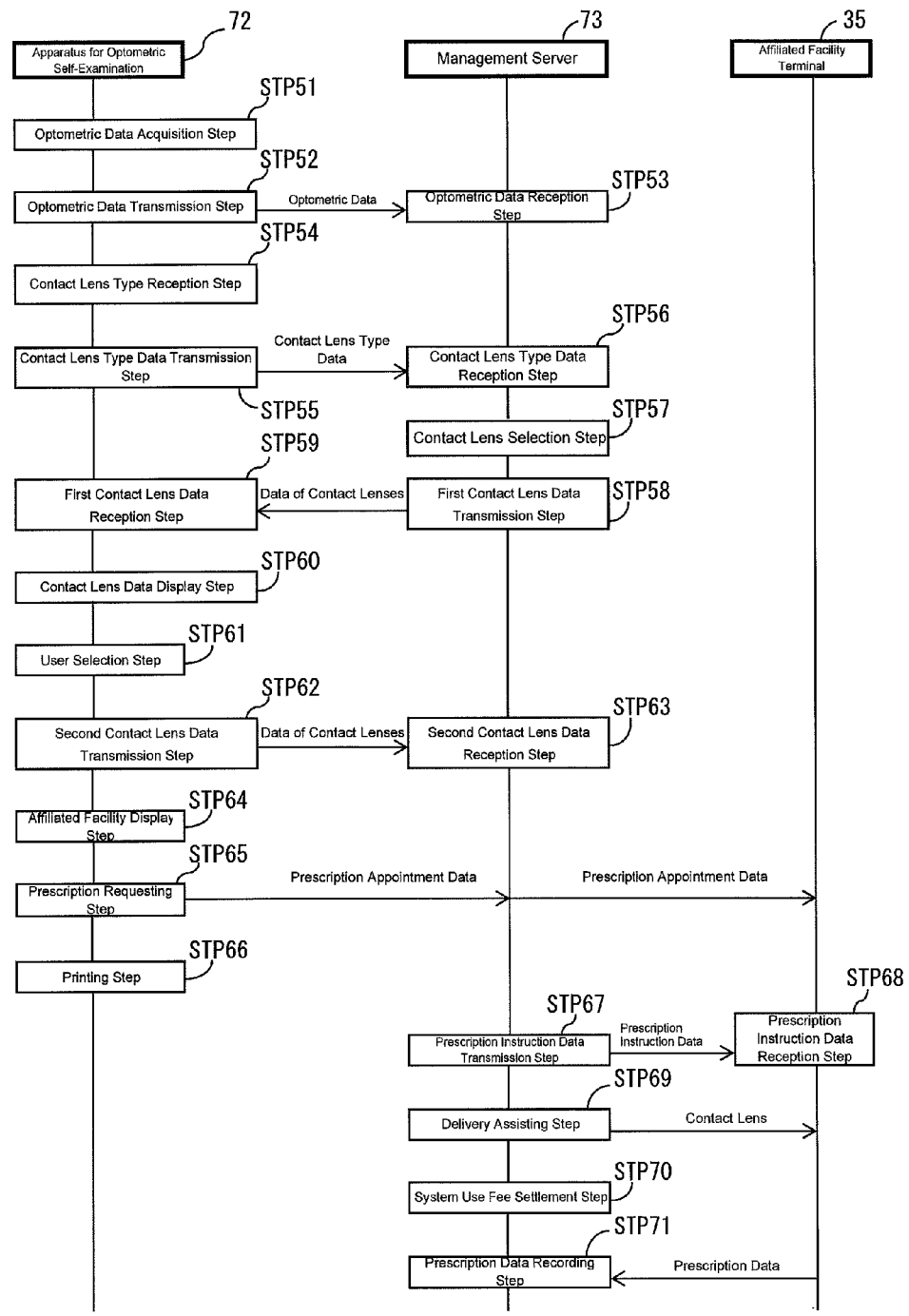
FIG. 12 is a sequence diagram illustrating an operational procedure of the contact lens selection system shown in FIG. 10.

Referring to FIG. 12, an operational procedure of the contact lens selection system 71 will be explained.

An optometric data acquisition step (STP 51) is a step of determining a shape of a cornea of a user in response to an operation by the user and acquiring corneal shape data of the user as optometric data. STP 51 is executed by the optometric data acquisition unit 55. STP 51 is executed according to a procedure similar to a procedure in STP 31.

An optometric data transmission step (STP 52) is a step of transmitting the optometric data acquired in STP 51 to the management server 73 in relationship to the user identification data of the user. STP 52 is executed by the communication unit 74. In STP 52, the communication unit 74 transmits the user ID code to identify the user entered by the user via the touchscreen 103 and the optometric data acquired in STP 51 to the management server 73 in relationship to each other. It is to be noted that in STP 52, the user ID code entered by the user is not necessarily transmitted, and a user ID code stored in advance as the user identification data 20 and received from the management server 73 may be transmitted.

An optometric data reception step (STP 53) is a step of receiving the optometric data and the user identification data transmitted in STP 52. STP 53 is executed by the communication unit 77.

A contact lens type reception step (STP 54) is a step of receiving a contact lens type desired by the user. STP 54 is executed by the contact lens type reception unit 16. STP 54 is executed according to a procedure similar to a procedure in STP 12.

A contact lens type data transmission step (STP 55) is a step of transmitting the contact lens type data received in STP 54 to the management server 73. STP 55 is executed by the communication unit 74.

A contact lens type data reception step (STP 56) is a step of receiving the contact lens type data transmitted in STP 55. STP 56 is executed by the communication unit 77.

A contact lens selection step (STP 57) is a step of selecting one or a plurality of contact lenses that match the contact lens type data received in STP 56 and suited for the user. In STP 57, contact lenses are selected after a correction is made with respect to each user based on the data recorded by the prescription data recording unit 79. STP 57 is executed by the contact lens selection unit 78. Specifically, the contact lens selection unit 78 first calculates, from the corneal shape data of the user received in STP 53 and the data of a base curve of a plurality of contact lenses stored in the database 81 as the shape data of contact lenses 8, a plurality of distances along normal lines to the back face of the contact lens respectively drawn from a plurality of points on the surface of the cornea of the user. The contact lens selection unit 78 selects (primarily selects), as the base curve of the contact lens suited for the user, a base curve that gives a small difference between these distances along the normal directions.

Next, the contact lens selection unit 78 determines a dioptric power of the contact lenses such as a spherical dioptric power and an astigmatic dioptric power based on the eye refractive index data received in STP 53. Moreover, the contact lens selection unit 78 may calculate spatial data of a space formed between the surface of the cornea of the user and the back face of the contact lens from a plurality of distances along normal lines to the back face of the contact lens respectively drawn from a plurality of points on the surface of the cornea of the user, acquire the spatial data as data of a lacrimal fluid layer formed between the surface of the cornea of the user and the back face of the contact lens, and determine the dioptric power of the contact lenses in light of the shape of the lacrimal fluid layer. Such a method for determining a dioptric power of the contact lenses is exemplified by a method including assuming that an air layer, a contact lens layer, a lacrimal fluid layer and the cornea respectively constitute a lens group, simulating a total aberration in use of the contact lens and determining a spherical dioptric power and an astigmatic dioptric power of a contact lens suitable for the user based on a result of such a simulation.

Furthermore, the contact lens selection unit 78 may calculate a refraction value in a state of the contact lens being applied to the eye by the user (over-refraction value) based on the optometric data, the spatial data and the shape data of the contact lens selected. In addition, the contact lens selection unit 78 may simulate visual performances in use of the contact lens based on the over-refraction value.

Moreover, the contact lens selection unit 78 determines a diameter of the contact lens based on the data of the transverse corneal diameter received in STP 53. For example, in the case of hard contact lenses, the contact lens selection unit 78 defines as the diameter of the contact lens a value obtained by subtracting about 1.5 to 2.5 mm from the value of the data of the transverse corneal diameter received in STP 53.

It is to be noted that the database 81 may store, as the shape data 8 of contact lenses, a shape of a bevel of a plurality of contact lenses, and the contact lens selection unit 78 may select a contact lens in light of the shape of the bevel.

Subsequently, the contact lens selection unit 78 calculate, based on prescription data 82 that include accumulated results of prescriptions executed in the past with respect to the user, an average of errors between values of the base curve of the primarily selected contact lenses and values of the base curve of the contact lenses actually and finally decided to be prescribed in the affiliated facility. Such an average of the errors can be determined from an averaged error 82*a* of the prescription data 82. The contact lens selection unit 78 corrects a value of the base curve of the primarily selected contact lenses by such an average of the errors, and selects (finally selects) one or a plurality of final contact lenses suited for the user. It is to be noted that such a correction may be made to the dioptric power, the diameter and the like of the contact lens in addition to the base curve of the contact lens.

Subsequently, the contact lens selection unit 78 selects, from among the contact lenses that match the contact lens type data received in STP 56, one or a plurality of contact lenses suited for a shape of the finally selected contact lens as a contact lens that matches the user, with reference to the shape data of contact lenses 8 and the contact lens type data 19.

A first contact lens data transmission step (STP 58) is a step of transmitting the data of the contact lenses selected in STP 57 to the apparatus for optometric self-examination 72. STP 58 is executed by the communication unit 77.

A first contact lens data reception step (STP 59) is a step of receiving the data of the contact lenses transmitted in STP 58. STP 59 is executed by the communication unit 74.

A contact lens data display step (STP 60) is a step of displaying the data of one or a plurality of contact lenses received in STP 59. STP 60 is executed by the contact lens data display unit 56. STP 60 is executed according to a procedure similar to a procedure in STP 40.

A user selection step (STP 61) is a step of allowing the user to select any contact lens from among one or a plurality of contact lenses displayed in STP 60. STP 61 is executed by the user selection unit 5. STP 61 is executed according to a procedure similar to a procedure in STP 4.

A second contact lens data transmission step (STP 62) is a step of transmitting the data of the contact lenses selected in STP 61 to the management server 73 in relationship to the user identification data 20 of the user stored in the database 81 or entered by the user. STP 62 is executed by the communication unit 74.

A second contact lens data reception step (STP 63) is a step of receiving the data of the contact lenses and the user identification data 20 transmitted in STP 62. STP 63 is executed by the communication unit 77.

An affiliated facility display step (STP 64) is a step of displaying the data of the affiliated facilities associated with the affiliated facility terminal 35. STP 64 is executed by the affiliated facility display unit 76. In STP 64, when an instruction to display affiliated facilities capable of prescribing a contact lens is conveyed from the user to the affiliated facility display unit 76 through touching of the touchscreen 103, the affiliated facility display unit 76 acquires affiliated facility data 44 stored in the database 81, and displays data of the affiliated facilities associated with the affiliated facility terminal 35 on the touchscreen 103. Such data of the affiliated facilities are exemplified by an affiliated facility name, an address, contact information, an eye care practitioner who belongs to the affiliated facility, a fee structure including a charge of a contact lens, and the like. It is to be noted that the touchscreen 103 may be configured to display affiliated facility names and the like in a list, to display only affiliated facilities in a specific area or affiliated facilities that charge a certain level of prescription fee or less according to the user's instruction and the like, or alternatively to display affiliated facilities near the installation site of the apparatus for optometric self-examination 72 intensively.

A prescription requesting step (STP 65) is a step of requesting for a prescription with the affiliated facility displayed in STP 64 in response to an operation by the user. STP 65 is executed by the prescription requesting unit 40. STP 65 is executed according to a procedure similar to a procedure in STP 21.

A printing step (STP 66) is a step of printing the optometric data acquired in STP 51 and the data of the contact lenses received in STP 59. STP 66 is executed by the printing unit 57. STP 66 is executed according to a procedure similar to a procedure in STP 44.

A prescription instruction data transmission step (STP 67) is a step of transmitting prescription instruction data produced based on the optometric data received in STP 53 and the data of the contact lenses selected in STP 57 to the affiliated facility terminal 35 in an affiliated facility in which a prescription is executed. STP 67 is executed by the communication unit 77. STP 67 is executed according to a procedure similar to a procedure in STP 45.

A prescription instruction data reception step (STP 68) is a step of receiving the prescription instruction data transmitted in STP 67. STP 68 is executed by the communication unit 49.

A delivery assisting step (STP 69) is a step of executing a delivery procedure to deliver a contact lens corresponding to the prescription instruction data transmitted in STP 67 to the affiliated facility that received the request in STP 65. STP 69 is executed by the delivery assistance unit 47. STP 69 is executed according to a procedure similar to a procedure in STP 25.

A system use fee settlement step (STP 70) is a step of executing a settlement procedure for a system use fee including a use fee for the apparatus for optometric self-examination 72 and a purchase price of the contact lens obtained through the contact lens selection system 71 under assumption of a lump sum payment thereof. STP 70 is executed by the system use fee settlement unit 80. Specifically, the system use fee settlement unit 80 displays on the touchscreen 103 a use fee for the apparatus for optometric self-examination 72 set in accordance with the content of the service and the like and a purchase cost of a contact lens in an affiliated facility set based on the prescription instruction data produced by the management server 73 and the like. If the system use fee settlement unit 80 receives approval of payment for the system use fee displayed on the touchscreen 103 from the user via the touchscreen 103, the system use fee settlement unit 80 executes a settlement procedure under assumption of the payment on the date scheduled for prescription by way of the prescription requesting unit 40. Such a system use fee including the use fee for the apparatus for optometric self-examination 72 and the purchase price of the contact lens obtained via the contact lens selection system 71 is collected in a lump sum by an administrator of the management server 73.

A prescription data recording step (STP 71) is a step of recording the data of the contact lenses primarily selected in STP 57 and the data of prescription executed by the affiliated facility that received the request for prescription in STP 65 in relationship to the user identification data. STP 71 is executed by the prescription data recording unit 79. In STP 71, the prescription data recording unit 79 first records in the database 81 a value of the base curve of the contact lenses primarily selected in STP 57 (primary selection value) in relationship to the user ID code of the user. Next, the prescription data recording unit 79 records in the database 81 a value of a base curve of the contact lens decided to be prescribed in the affiliated facility that received the request for prescription in STP 65 (prescription decision value) and the affiliated facility ID code of the affiliated facility in relationship to the user ID code and the primary selection value recorded first. These data recorded in STP 71 are organized with respect to each user ID code, and stored in the database 81 as the prescription data 82 of each user. It is to be noted that in STP 71, the respective data stored as the prescription data 82 do not need to be stored at the same time, and it is possible, for example, that the user ID code and the primary selection value are recorded after STP 57 and the prescription decision value and the affiliated facility ID code of the affiliated facility are recorded after STP 70.

It is to be noted that the contact lens selection system 71 may be constructed to receive from the user a reply to the medical interview data displayed by the medical interview unit 50 (medical interview step) instead of executing each step described above or according to the user's choice, as long as the user who has utilized the contact lens selection system 71 within a predetermined period of time and has purchased or been prescribed with a contact lens. In this case, if the user's reply to the medical interview data meets prerequisites, the medical interview unit 50 transmits the user ID code of the user and the data of the contact lens prescribed for the user last time to the delivery assistance unit 47 in relationship to each other. Further, if the user ID code and the data of the contact lens prescribed for the user last time are transmitted, the delivery assistance unit 47 executes a delivery procedure to deliver a contact lens corresponding to the data of the contact lens to the user.

The contact lens selection system 71 is readily available to even a new user through the user's own operation, and the user can find a contact lens suitable for the user. According to the contact lens selection system 71, since the contact lens selection unit 78 selects one or a plurality of contact lenses that match the user based on the shape data 8 of a plurality of contact lenses stored in the database 81, lack of an eye care practitioner's skill can favorably compensated for by storing in the database 81 shape data of various contact lenses such as soft contact lenses and hard contact lenses, and a contact lens suitable for the user can be provided. According to the contact lens selection system 71, if an affiliated facility in which a prescription is executed utilizes the prescription instruction data transmitted by the prescription instruction data transmission unit, a reduction of a time period required for the prescription for the user and sophistication of the prescription for the user can be achieved, and additionally a process of purchase of a contact lens by the user can proceed smoothly.

According to the contact lens selection system 71, since the contact lens selection unit 78 can make a correction with respect to each user based on the data recorded by the prescription data recording unit 79, so far as a user who uses the contact lens selection system 71 more than once is concerned, fitting properties of the contact lenses selected by the contact lens selection unit 79 can be further improved.

The contact lens selection system 71 can execute, via the system use fee settlement unit 80, a settlement procedure for a system use fee including a use fee for the apparatus for optometric self-examination 72 and a purchase price of a contact lens obtained via the contact lens selection system 71. Therefore, according to the contact lens selection system 71, the user can proceed with a payment procedure collectively at an appropriate time, and consequently the efficiency of the settlement procedure can be promoted.

Moreover, according to the contact lens selection system 71, the use fee for the apparatus for optometric self-examination 72, and the purchase price of the contact lens registered via the delivery assistance unit 47 and delivered to the affiliated facility can be collected in a lump sum using the system use fee settlement unit 80. Therefore, according to the contact lens selection system 71, a selling system can be easily and reliably constructed in which an administrator of the management server 73 directly sells a contact lens arranged by the delivery assistance unit 47 to be delivered and the administrator pays a predetermined commission to the affiliated facility. As a result, according to the contact lens selection system 71, easiness and reliability of an inventory control of contact lenses centered on the management server 73, and the like can be improved, and additionally excess or shortage of stocks in an affiliated facility can be effectively resolved.

It is to be noted that the apparatus for optometric self-examination, the management server and the contact lens selection system according to the present invention may be exploited in various modified or improved embodiments other than those as described above. For example, the apparatus for optometric self-examination, the management server and the contact lens selection system according to the present invention can provide various embodiments by an appropriate combination of a plurality of constitutive elements disclosed in the above embodiments. Moreover, the basic data measurement terminal and the user operation terminal according to the present invention may be each independently present, and for example, the basic data measurement terminal does not need to receive the user's instruction via the touchscreen.

According to the apparatus for optometric self-examination, it is possible that the optometric data acquisition unit acquires corneal shape data of the user as the optometric data, the contact lens selection unit calculates a distance from cornea surface to the back face of the contact lens along a normal direction based on corneal shape data and data of the shape of the contact lens and select a contact lens, based on the normal direction distance. Accordingly, fitting properties of the selected contact lens to the user can be further improved.

According to the apparatus for optometric self-examination, it is possible that the prescription data recording unit records data of contact lenses selected by the contact lens selection unit and data of a prescription executed in an affiliated facility in relationship to user identification data, and the contact lens selection unit makes a correction with respect to each user based on the data recorded by the prescription data recording unit. Accordingly, so far as a user who uses the apparatus for optometric self-examination more than once is concerned, fitting properties of the contact lenses selected by the contact lens selection unit can be further improved.

The apparatus for optometric self-examination may be configured to be able to receive a payment by credit card in addition to or in place of a cash payment.

According to the management server, it is possible that the optometric data reception unit receives curvature data at a plurality of points on the surface of the cornea of the user, and the contact lens selection unit calculates an average value from the maximum value and the minimum value among the curvature data and select a contact lens based on the average value. Accordingly, by obtaining a plurality of curvature data of the surface of the cornea of the user, a contact lens suitable for the user can be easily and rapidly selected.

According to the management server, the contact lens selection unit may select a contact lens after making a correction based on a value obtained by subtracting the minimum value from the maximum value among the curvature data at the plurality of points acquired as the optometric data. Accordingly, fitting properties of the selected contact lens to the user can be improved.

Moreover, even in the case in which the contact lens selection unit makes a correction based on the data recorded by the prescription data recording unit, the contact lens selection unit does not necessarily have to make a correction based on an average of errors between values of the base curve of the primarily selected contact lenses and values of the base curve of the contact lenses actually and finally decided to be prescribed in the affiliated facility, and may make a correction based on a certain, arbitrarily predetermined error such as the latest error data.

Furthermore, in regard to a method in which the contact lens selection unit calculates the average value from the maximum value and the minimum value among the curvature data at the plurality of points acquired as the optometric data and selects a contact lens based on the average value, it is possible to compare such an average value and a value of a base curve of the contact lens and select, as a contact lens suitable for the user, a contact lens that gives a small difference therebetween.

The shape data of contact lenses, the user identification data, the affiliated facility data, the prescription data and the like that are employed in the present invention do not necessarily have to be stored in a specific apparatus (such as the apparatus for optometric self-examination, the management server and the affiliated facility terminal), and may be data transmitted and received by other external apparatuses and the like.

The contact lens selection system does not necessarily have to select a contact lens that is purchased by a user after a prescription of an affiliated facility or the like, and may be configured to invite the user to purchase the contact lenses selected by the contact lens selection unit. Moreover, in this case, the contact lens selection system may acquire data of the user's home, workplace or the like as data of a destination of the contact lens, and execute a procedure to deliver the contact lens to the destination.

According to the contact lens selection system, the apparatus for optometric self-examination may carry a plurality of contact lenses in stock. Furthermore, the contact lens selection system may be configured to provide the user with a contact lens carried by the apparatus for optometric self-examination in stock if the reply from the user to the medical interview data displayed by the medical interview unit meets prerequisites. Moreover, the contact lens selection system may be configured such that medical interview data can be acquired from a commercially available personal computer, and a reply to the medical interview data can be sent from the commercially available personal computer.

The contact lens selection system may be configured to inform the user of an installation site of an apparatus for optometric self-examination on a specific website. Accordingly, convenience for a user can be further enhanced. The contact lens selection system may be configured such that predetermined data such as user identification data can be entered (registered) on the Web. Accordingly, a procedure executed on the apparatus for optometric self-examination can be simplified. According to the contact lens selection system, the contact lens data display unit may display grounds for recommendation of each contact lens and characteristics of each contact lens such as advantages and disadvantages thereof. Moreover, these grounds for recommendation may be decided based on a lifestyle proposal of the user, a result of a medical interview, or the like.

A commercially available personal computer and the like can be used as the apparatus for optometric self-examination according to the present invention, as long as the commercially available personal computer and the like satisfy the aforementioned features.

INDUSTRIAL APPLICABILITY

As set forth above, the apparatus for optometric self-examination, the management server and the contact lens selection system according to the present invention can shorten a time period required by an eye care practitioner for prescription, or even if no eye care practitioner's prescription is provided, allow for easy and reliable selection of a contact lens preferred for a user. Therefore, the apparatus for optometric self-examination according to the present invention is suitable for installation inside or outside a contact lens store, a glasses shop, an ophthalmic facility, a drug store, a station, a convenience store and the like, in that a user is accessible to the apparatus for optometric self-examination whether the user is a new user or a repeater.

EXPLANATION OF THE REFERENCE SYMBOLS 1 apparatus for optometric self-examination
2 optometric data acquisition unit
3 contact lens data display unit
4 contact lens selection unit
5 user selection unit
6 printing unit
7 database
8 shape data of contact lenses
11 contact lens selection system
12 apparatus for optometric self-examination
13 network
14 management server
15 communication unit
16 contact lens type reception unit
17 contact lens selection unit
18 database
19 contact lens type data
20 user identification data
21 communication unit
31 contact lens selection system
32 apparatus for optometric self-examination
33 network
34 management server
35 affiliated facility terminal
36 communication unit
37 display unit
38 affiliated facility display unit
39 contact lens selection unit
40 prescription requesting unit
41 printing unit
42 prescription data recording unit
43 database
44 affiliated facility data
45 prescription data
46 communication unit
47 delivery assistance unit
48 use fee settlement unit
49 communication unit
50 medical interview unit
51 contact lens selection system
52 apparatus for optometric self-examination
53 management server
54 communication unit
55 optometric data acquisition unit
56 contact lens data display unit
57 printing unit
58 database
59 communication unit
60 contact lens selection unit
61 database
71 contact lens selection system
72 apparatus for optometric self-examination
73 management server
74 communication unit
75 display unit
76 affiliated facility display unit
77 communication unit
78 contact lens selection unit
79 prescription data recording unit
80 system use fee settlement unit
81 database
82 prescription data
101 basic data measurement terminal
102 user operation terminal
103 touchscreen
104 paper ejection unit
105 chair

The invention claimed is:

1. An apparatus for optometric self-examination, comprising:
a database to store shape data of a plurality of contact lenses;
an optometric data acquisition unit for determining at least a part of a shape of a cornea of a user in response to an operation by the user and acquiring optometric data, based on the shape of the cornea;
a contact lens selection unit for selecting one or a plurality of contact lenses suited for the optometric data, based on the optometric data and the shape data of contact lenses stored in the database; and
a contact lens data display unit for displaying a result of selection of a contact lens selected by the contact lens selection unit,
wherein the optometric data acquisition unit acquires curvature data at a plurality of points on a surface of the cornea of the user the optometric data, and
the contact lens selection unit calculates an average value from a maximum value and a minimum value among the curvature data at the plurality of points acquired as the optometric data and selects the one or a plurality of contact lenses based on the average value.

2. The apparatus for optometric self-examination according to claim 1, wherein the contact lens selection unit selects the one or a plurality of contact lenses after making a correction based on a value obtained by subtracting the minimum value from the maximum value among the curvature data at the plurality of points acquired as the optometric data.

3. The apparatus for optometric self-examination according to claim 1, wherein
the optometric data acquisition unit acquires eye refractive index data of the user, and
the contact lens selection unit determines a dioptric power of the contact lenses based on the eye refractive index data.

4. The apparatus for optometric self-examination according to claim 3, wherein the contact lens selection unit calculates spatial data of a space formed between a surface of the cornea of the user and the back face of the contact lens, based on the optometric data and the shape data of contact lenses, thereafter acquires data of a lacrimal fluid layer formed between the surface of the cornea of the user and the back face of the contact lens, based on the spatial data, and determines the dioptric power of the contact lens in light of a shape of the lacrimal fluid layer.

5. The apparatus for optometric self-examination according to claim 4, wherein the contact lens data display unit displays a fluorescein pattern representing the shape of the lacrimal fluid layer.

6. The apparatus for optometric self-examination according to claim 4, wherein
the contact lens selection unit calculates a refraction value in a state of the contact lens being applied to the eye (over-refraction value) based on the optometric data, the spatial data and shape data of the contact lens selected, and
the contact lens data display unit displays the over-refraction value.

7. The apparatus for optometric self-examination according to claim 6, wherein
the contact lens selection unit simulates visual performances in use of the contact lens based on the over-refraction value, and
the contact lens data display unit displays a result of simulation of the visual performances.

8. The apparatus for optometric self-examination according to claim 1, wherein
the optometric data acquisition unit acquires data of a transverse corneal diameter of the user, and
the contact lens selection unit determines a diameter of the contact lens based on the data of the transverse corneal diameter.

9. The apparatus for optometric self-examination according to claim 1, further comprising:
an affiliated facility display unit for displaying data of a plurality of affiliated facilities capable of prescribing a contact lens; and
a prescription requesting unit for allowing the user to select any affiliated facility from among the affiliated facilities displayed by the affiliated facility display unit and to request for a prescription with the affiliated facility in response to an operation by the user.

10. The apparatus for optometric self-examination according to claim 9, wherein
the apparatus for optometric self-examination further comprises a prescription data recording unit for recording a correlation between the data of the contact lenses selected by the contact lens selection unit and data of the prescription executed by the affiliated facility that received a request from the prescription requesting unit, and
the contact lens selection unit selects the one or a plurality of contact lenses after making a correction based on the data recorded by the prescription data recording unit.

11. The apparatus for optometric self-examination according to claim 10, wherein
the prescription data recording unit records the data of the contact lenses selected by the contact lens selection unit and the data of the prescription executed by the affiliated facility, in relationship to user identification data, and
the contact lens selection unit makes a correction with respect to each user based on the data recorded by the prescription data recording unit.

12. An apparatus for optometric self-examination comprising:
a database to store shape data of a plurality of contact lenses;
an optometric data acquisition unit for determining at least a part of a shape of a cornea of a user in response to an operation by the user and acquiring optometric data, based on the shape of the cornea;
a contact lens selection unit for selecting one or a plurality of contact lenses suited for the optometric data, based on the optometric data and the shape data of contact lenses stored in the database; and
a contact lens data display unit for displaying a result of selection of a contact lens selected by the contact lens selection unit,
wherein the optometric data acquisition unit acquires corneal shape data of the cornea of the user as the optometric data, and
the contact lens selection unit calculates a distance from a cornea surface to a back face of the contact lens along a normal direction, based on the corneal shape data and the shape data of contact lenses, and selects the one or a plurality of contact lenses based on the distance along the normal direction.

13. A management server capable of communicating with an apparatus for optometric self-examination via a network,
the apparatus for optometric self-examination comprising:
an optometric data acquisition unit for determining at least a part of a shape of a cornea of a user in response to an operation by the user and acquiring optometric data, based on the shape of the cornea;
an optometric data transmission unit for transmitting via a network the optometric data acquired by the optometric data acquisition unit relationship to user identification data; and
a contact lens data display unit for displaying a result of selection of a contact lens suited for the optometric data, based on the optometric data and shape data of contact lenses, and
the management server comprising:
a database to store shape data of a plurality of contact lenses;
an optometric data reception unit for receiving the optometric data and user identification data transmitted from the apparatus for optometric self-examination;
a contact lens selection unit for selecting one or a plurality of contact lenses suited for the optometric data, based on the optometric data and the shape data of contact lenses stored in the database; and
a first contact lens data transmission unit for transmitting data of the contact lenses selected by the contact lens selection unit to the apparatus for optometric self-examination,
wherein the optometric data reception unit receives the curvature data at the plurality of points on a surface of the cornea of the user, and
the contact lens selection unit calculates an average value from a maximum value and a minimum value among the curvature data at the plurality of points and selects the one or a plurality of contact lenses based on the average value.

14. The management server according to claim 13, wherein the contact lens selection unit selects the one or a plurality of contact lenses after making a correction based on a value obtained by subtracting the minimum value from the maximum value among the curvature data at the plurality of points acquired as the optometric data.

15. The management server according to claim 13, wherein the contact lens selection unit calculates spatial data of a space formed between the surface of the cornea of the user and the back face of the contact lens, based on the optometric data and the shape data of contact lenses, thereafter acquires data of a lacrimal fluid layer formed between the surface of the cornea of the user and the back face of the contact lens, based on the spatial data, and determines the dioptric power of the contact lens in light of a shape of the lacrimal fluid layer.

16. The management server according to claim 15, wherein the first contact lens data transmission unit transmits a fluorescein pattern representing a shape of the lacrimal fluid layer to the apparatus for optometric self-examination.

17. The management server according to claim 15, wherein the contact lens selection unit calculates a refraction value in a state of the contact lens being applied to the eye (over-refraction value) based on the optometric data, the spatial data and the shape data of the contact lens selected, and the first contact lens data transmission unit transmits the over-refraction value to the apparatus for optometric self-examination.

18. The management server according to claim 17, wherein the contact lens selection unit simulates visual performances in use of the contact lens based on the over-refraction value, and
the first contact lens data transmission unit transmits data of a result of simulation of the visual performances to the apparatus for optometric self-examination.

19. The management server according to claim 13, wherein the optometric data reception unit receives data of a transverse corneal diameter of the user, and
the contact lens selection unit determines a diameter of the contact lens based on the data of the transverse corneal diameter.

20. A management server capable of communicating with an apparatus for optometric self-examination via a network, the apparatus for optometric self-examination comprising:
an optometric data acquisition unit for determining at least a part of a shape of a cornea of a user in response to an operation by the user and acquiring optometric data, based on the shape of the cornea;
an optometric data transmission unit for transmitting via a network the optometric data acquired by the optometric data acquisition unit in relationship to user identification data; and
a contact lens data display unit for displaying a result of selection of a contact lens suited for the optometric data, based on the optometric data and shape data of contact lenses, and
the management server comprising:
a database to store shape data of a plurality of contact lenses;
an optometric data reception unit for receiving the optometric data and user identification data transmitted from the apparatus for optometric self-examination;
a contact lens selection unit for selecting one or a plurality of contact lenses suited for the optometric data, based on the optometric data and the shape data of contact lenses stored in the database; and
a first contact lens data transmission unit for transmitting data of the contact lenses selected by the contact lens selection unit to the apparatus for optometric self-examination,
wherein the optometric data reception unit receives corneal shape data of the user, and
the contact lens selection unit calculates a distance from cornea surface to a back face of the contact lens along a normal direction based on the corneal shape data and the shape data of contact lenses, and selects the one or a plurality of contact lenses, based on the distance along the normal direction.

\* \* \* \* \*